(12) United States Patent
Itoi et al.

(10) Patent No.: US 10,147,886 B2
(45) Date of Patent: *Dec. 4, 2018

(54) ORGANIC ELECTROLUMINESCENT MATERIAL AND ORGANIC ELECTROLUMINESCENT DEVICE INCLUDING THE SAME

(71) Applicant: SAMSUNG DISPLAY CO., LTD., Yongin-si, Gyeonggi-do (KR)

(72) Inventors: Hiroaki Itoi, Yokohama (JP); Nobutaka Akashi, Yokohama (JP)

(73) Assignee: Samsung Display Co., Ltd., Yongin-Si, Gyeonggi-do (KR)

( * ) Notice: Subject to any disclaimer, the term of this patent is extended or adjusted under 35 U.S.C. 154(b) by 352 days.

This patent is subject to a terminal disclaimer.

(21) Appl. No.: 14/875,312

(22) Filed: Oct. 5, 2015

(65) Prior Publication Data
US 2016/0099420 A1    Apr. 7, 2016

(30) Foreign Application Priority Data

Oct. 6, 2014  (JP) ................ 2014-205417

(51) Int. Cl.
*H01L 51/00* (2006.01)
*C07D 333/76* (2006.01)
*H01L 51/50* (2006.01)

(52) U.S. Cl.
CPC ........ *H01L 51/0061* (2013.01); *C07D 333/76* (2013.01); *H01L 51/006* (2013.01);
(Continued)

(58) Field of Classification Search
CPC . C07D 333/76; H01L 51/0059; H01L 51/006; H01L 51/0061; H01L 51/0074; H01L 51/0081; H01L 5/5056; C09K 11/06
See application file for complete search history.

(56) References Cited

U.S. PATENT DOCUMENTS 9,590,186 B2 *  3/2017  Itoi ................. H01L 51/0073
9,871,204 B2 *  1/2018  Fuchiwaki ......... H01L 51/0061
(Continued)

FOREIGN PATENT DOCUMENTS

JP    2006-151844 A  *  6/2006
JP    2009-029726 A     2/2009
(Continued)

OTHER PUBLICATIONS

Machine translation for JP 2006-151844 A (publication date Jun. 2006). (Year: 2006).*

*Primary Examiner* — Dawn L Garrett
(74) *Attorney, Agent, or Firm* — Lee & Morse, P.C.

(57) ABSTRACT

An organic electroluminescent (EL) material and an organic EL device, the material being represented by the following Formula 1:

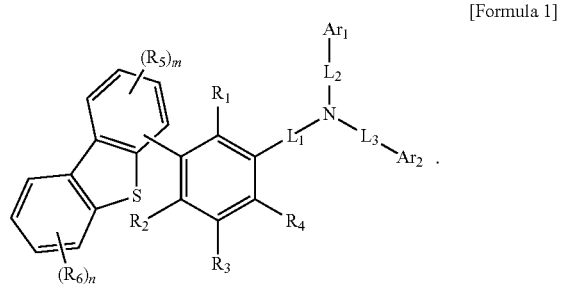

[Formula 1]

3 Claims, 2 Drawing Sheets

(52) U.S. Cl.
CPC ...... *H01L 51/0059* (2013.01); *H01L 51/0074* (2013.01); *H01L 51/0081* (2013.01); *H01L 51/5056* (2013.01)

(56) References Cited

U.S. PATENT DOCUMENTS

| | | | | |
|---|---|---|---|---|
| 9,902,901 B2* | 2/2018 | Matsuura | ............ | C09K 11/025 |
| 10,014,477 B2 | 7/2018 | Kato et al. | | |
| 2007/0278938 A1* | 12/2007 | Yabunouchi | ......... | C07D 307/91 313/504 |
| 2009/0017330 A1* | 1/2009 | Iwakuma | ............... | C09K 11/06 428/690 |
| 2011/0248246 A1* | 10/2011 | Ogita | ................... | C07D 307/91 257/40 |
| 2012/0097937 A1* | 4/2012 | Iwakuma | ............... | C09K 11/06 257/40 |
| 2014/0027747 A1* | 1/2014 | Mun | ..................... | H01L 51/006 257/40 |
| 2014/0197402 A1* | 7/2014 | Huh | .................... | H01L 51/0061 257/40 |
| 2015/0179951 A1* | 6/2015 | Fuchiwaki | .......... | H01L 51/0061 257/40 |
| 2016/0133848 A1* | 5/2016 | Balaganesan | ........ | C07D 333/76 257/40 |

FOREIGN PATENT DOCUMENTS

| | | |
|---|---|---|
| JP | 2009-267255 A | 11/2009 |
| JP | 2011-051936 A | 3/2011 |
| JP | 2011-231108 A | 11/2011 |
| JP | 2013-028597 A | 2/2013 |
| JP | 2014-065885 A | 4/2014 |
| WO | WO 2009/008099 A1 | 1/2009 |
| WO | WO 2011/021520 A1 | 2/2011 |
| WO | WO 2012/096263 A1 | 7/2012 |
| WO | WO 2012/134203 A2 | 10/2012 |
| WO | WO 2013/036043 A2 | 3/2013 |
| WO | WO 2014/034795 A1 | 3/2014 |
| WO | WO 2014/129846 A1 | 8/2014 |

* cited by examiner

ORGANIC ELECTROLUMINESCENT MATERIAL AND ORGANIC ELECTROLUMINESCENT DEVICE INCLUDING THE SAME

CROSS-REFERENCE TO RELATED APPLICATION

Japanese Patent Application No. 2014-205417, filed on Oct. 6, 2014, in the Japanese Patent Office, and entitled: "Organic Electroluminescent Material and Organic Electroluminescent Device Including the Same," is incorporated by reference herein in its entirety.

BACKGROUND

1. Field

Embodiments relate to an organic electroluminescent material and an organic electroluminescent device including the same.

2. Description of the Related Art

Recently, the developments on organic electroluminescent (EL) displays are being actively conducted as image displays. The organic EL device is different from a liquid crystal display and is a self-luminescent display realizing display by recombining holes and electrons injected from an anode and a cathode and emitting light from a luminescent material including an organic material in an emission layer.

An organic EL device is known as, e.g., an organic device including an anode, a hole transport layer disposed on the anode, an emission layer disposed on the hole transport layer, an electron transport layer disposed on the emission layer and a cathode disposed on the electron transport layer. Holes are injected from the anode, and the injected holes are injected via the hole transport layer into the emission layer. Meanwhile, electrons are injected from the cathode, and the injected electrons are injected via the electron transport layer into the emission layer. Holes and electrons injected into the emission layer recombine to generate excitons in the emission layer. The organic EL device emits light using light generated by the radiation deactivation of the excitons. In addition, the configuration of the organic EL device is not limited to the above-described configuration, and various modifications are possible.

SUMMARY

Embodiments are directed to an organic electroluminescent material and an organic electroluminescent device including the same.

An embodiment may provide an organic EL material represent by the following Formula 1.

[Formula 1]

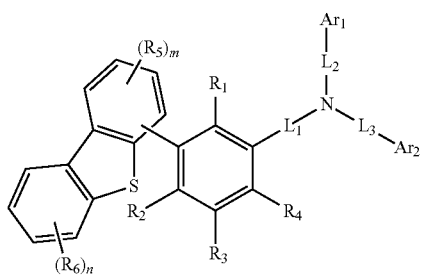

In Formula 1, $R_1$, $R_2$, $R_3$, $R_4$, $R_5$ and $R_6$ are each independently a substituted or unsubstituted aryl group having 6 to 30 ring carbon atoms or carbon atoms for forming a ring, a substituted or unsubstituted heteroaryl group having 1 to 30 carbon atoms for forming a ring, an alkyl group having 1 to 15 carbon atoms, a substituted or unsubstituted silyl group, a halogen atom, a hydrogen atom or a deuterium atom, $Ar_1$ and $Ar_2$ are each independently a substituted or unsubstituted aryl group having 6 to 30 carbon atoms for forming a ring, or a substituted or unsubstituted heteroaryl group having 1 to 30 carbon atoms for forming a ring, $L_1$, $L_2$ and $L_3$ are each independently a direct linkage, or a divalent group selected from the group consisting of a substituted or unsubstituted alkylene group having 1 to 30 carbon atoms, an aralkylene group, a substituted or unsubstituted arylene group, a substituted or unsubstituted heteroarylene group and a silyl group, m is an integer from 0 to 3, and n is an integer from 0 to 4.

In an embodiment, $Ar_1$ and $Ar_2$ may be each independently a phenyl group, a biphenyl group, a naphthyl group, a 4-(1-naphthyl)phenyl group, or a 4-(2-naphthyl)phenyl group in the organic EL material represented by Formula 1.

In an embodiment, an organic EL material represented by the following Formula 2 may be provided.

[Formula 2]

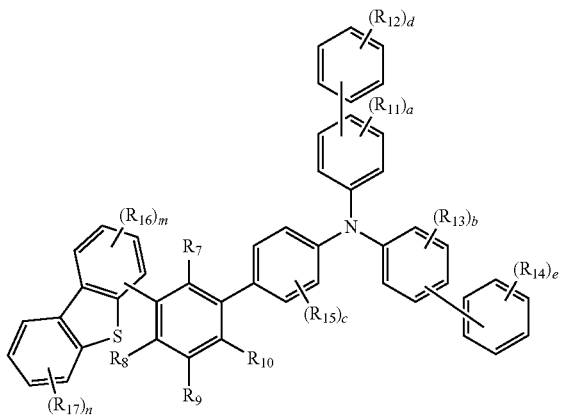

In Formula 2, $R_7$, $R_8$, $R_9$, $R_{10}$, $R_{11}$, $R_{12}$, $R_{13}$, $R_{14}$, $R_{15}$, $R_{16}$ and $R_{17}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a silyl group, a halogen atom, a hydrogen atom or a deuterium atom, a, b and c are each independently an integer from 0 to 4, d and e are each independently an integer from 0 to 5, m is an integer from 0 to 3, and n is an integer from 0 to 4.

In an embodiment, the organic EL material represented by Formula 2 may be an organic EL material represented by the following Formula 3.

[Formula 3]

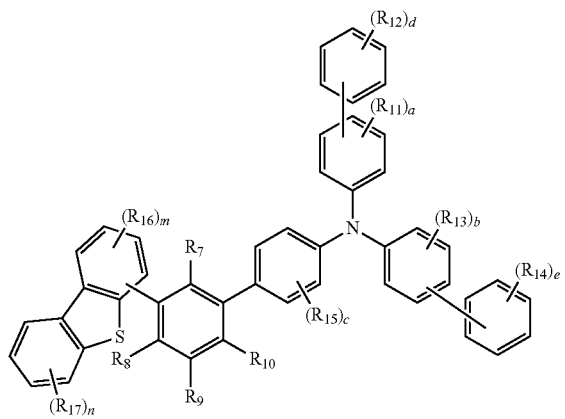

In an embodiment, an organic EL device may include one of the above-mentioned organic EL materials in at least one layer of stacking layers disposed between an emission layer and an anode.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
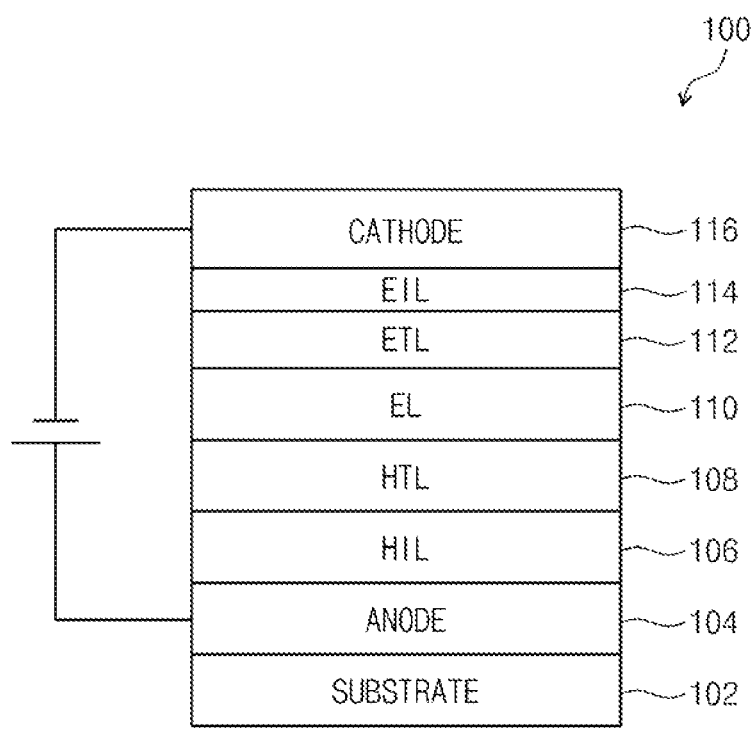
FIG. 1 illustrates a schematic diagram of an organic EL device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present. Like reference numerals refer to like elements throughout.

Long life and the high emission efficiency of an organic EL device may be obtained by employing a dibenzothiophene part at a meta position of a phenylene group combined with a nitrogen atom (N) of an amine directly or via a linker, thereby increasing charge mobility and improving heat-resistance and tolerance.

Hereinafter, the organic EL material and the organic EL device including the same according to an embodiment will be explained referring to attached drawings. The organic EL material and the organic EL device including the same according to an embodiment may, however, be embodied in different forms and should not be constituted as limited to the embodiments set forth herein. In addition, the same reference numeral may be designated to the same parts or parts having the same function in the drawing referred to in the embodiments, and the repeated explanation thereon may be omitted.

The organic EL material or compound according to an embodiment may include an amine compound introducing a dibenzothiophene part at the meta position of a phenylene group combined with amine. For example, the organic EL material may be represented by the following Formula 1.

[Formula 1]

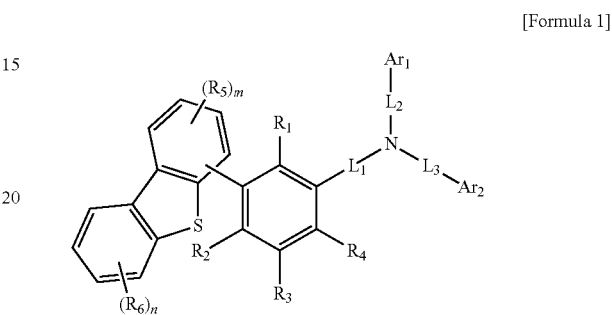

In the organic EL material represented by Formula 1, $R_1$, $R_2$, $R_3$, $R_4$, $R_5$ and $R_6$ may each independently be or include, e.g., a substituted or unsubstituted aryl group having 6 to 30 ring carbon atoms, a substituted or unsubstituted heteroaryl group having 1 to 30 ring carbon atoms, an alkyl group having 1 to 15 carbon atoms, a substituted or unsubstituted silyl group, a halogen atom, a hydrogen atom, or a deuterium atom, $Ar_1$ and $Ar_2$ may each independently be or include, e.g., a substituted or unsubstituted aryl group having 6 to 30 ring carbon atoms or a substituted or unsubstituted heteroaryl group having 1 to 30 ring carbon atoms, $L_1$ and $L_2$ may each independently be or include, e.g., a direct linkage (e.g., single bond), or a divalent group selected from the group of a substituted or unsubstituted alkylene group having 1 to 30 carbon atoms, an aralkylene group, a substituted or unsubstituted arylene group, a substituted or unsubstituted heteroarylene group and a silyl group, m may be an integer of 0 to 3, and n may be an integer of 0 to 4.

The substituted or unsubstituted aryl group having 6 to 30 ring carbon atoms of $R_1$, $R_2$, $R_3$, $R_4$, $R_5$ and $R_6$ in Formula 1 may include, e.g., a phenyl group, a naphthyl group, an anthracenyl group, a phenanthryl group, a biphenyl group, a terphenyl group, a quaterphenyl group, a quinqephenyl group, a sexiphenyl group, a fluorenyl group, a triphenylene group, a biphenylene group, a pyrenyl group, a benzofluoranthenyl group, a glyceryl group, or the like.

The substituted or unsubstituted heteroaryl group having 1 to 30 ring carbon atoms of $R_1$, $R_2$, $R_3$, $R_4$, $R_5$ and $R_6$ may include, e.g., a pyridyl group, a furyl group, a thienyl group, a quinolyl group, an isoquinolyl group, a benzofuryl group, a benzothienyl group, an indolyl group, a benzoxazolyl group, a benzothiazolyl group, a quinoxalyl group, a benzoimidazolyl group, a dibenzofuryl group, a dibenzothienyl group, a carbazolyl group, or the like.

The alkyl group having 1 to 15 carbon atoms of $R_1$, $R_2$, $R_3$, $R_4$, $R_5$ and $R_6$ may include, e.g., a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, an 1-hydroxyethyl group, a 2-hydroxyethyl group, a 2-hydroxyisobutyl group, an 1,2-dihydroxyethyl group, an 1,3-dihydroxyisopropyl group, a 2,3-dihydroxy-t-butyl group, an 1,2,3-trihydroxypropyl group, a chloromethyl group, an 1-chloroethyl group, a 2-chloroethyl group, a 2-chloroisobutyl group, an 1,2-dichloroethyl group, an 1,3-dichloroisopropyl group, a 2,3-dichloro-t-butyl group, an 1,2,3-trichloropropyl group, a bromomethyl group, an 1-bromoethyl group, a 2-bromoethyl group, a 2-bromoisobutyl group, an 1,2-dibromoethyl group, an 1,3-dibromoisopropyl group, a 2,3-dibromo-t-butyl group, an 1,2,3-tribromopropyl group, an iodomethyl group, an 1-iodoethyl group, a 2-iodoethyl group, a 2-iodoisobutyl group, an 1,2-diiodoethyl group, an 1,3-diiodoisopropyl group, a 2,3-diiodo-t-butyl group, an 1,2,3-triiodopropyl group, a cyanomethyl group, an 1-cyanoethyl group, a 2-cyanoethyl group, a 2-cyanoisobutyl group, an 1,2-dicyanoethyl group, an 1,3-dicyanoisopropyl group, a 2,3-dicyano-t-butyl group, an 1,2,3-tricyanopropyl group, a nitromethyl group, an 1-nitroethyl group, a 2-nitroethyl group, a 2-nitroisobutyl group, an 1,2-dinitroethyl group, an 1,3-dinitroisopropyl group, a 2,3-dinitro-t-butyl group, an 1,2,3-trinitropropyl group, a cyclopropyl group, a cyclobutyl group, a cyclopentyl group, a cyclohexyl group, a 4-methylcyclohexyl group, an 1-adamantyl group, a 2-adamantyl group, an 1-norbornyl group, a 2-norbornyl group, or the like.

The silyl group of $R_1$, $R_2$, $R_3$, $R_4$, $R_5$ and $R_6$ may include, e.g., a trialkylsilyl group, a triarylsilyl group, a monoalkyldiarylsilyl group and a dialkylmonoarylsilyl group, for example, a trimethylsilyl group, a triphenylsilyl group, or the like.

The halogen atom of $R_1$, $R_2$, $R_3$, $R_4$, $R_5$ and $R_6$ may include, e.g., a fluorine atom (F), a chlorine atom (Cl), and/or a bromine atom (Br).

In an implementation, $R_1$, $R_2$, $R_3$, $R_4$, $R_5$ and/or $R_6$ may include, e.g., a hydrogen atom or a deuterium atom.

In an implementation, neighboring ones of $R_2$, $R_3$, $R_4$, $R_5$ and $R_6$ may combine to each other to form a saturated or unsaturated ring.

In Formula 1, the substituted or unsubstituted aryl group having 6 to 30 ring carbon atoms of $Ar_1$ and $Ar_2$ may include, e.g., a phenyl group, a 1-naphthyl group, a 2-naphthyl group, a biphenyl group, a 4-(1-naphthyl)phenyl group, a 4-(2-naphthyl)phenyl group, of the like.

The substituted or unsubstituted heteroaryl group having 1 to 30 ring carbon atoms of $Ar_1$ and $Ar_2$ may include, e.g., a pyridyl group, a furyl group, a thienyl group, a quinolyl group, an isoquinolyl group, a benzofuryl group, a benzothienyl group, an indolyl group, a benzooxazolyl group, a benzothiazolyl group, a quinoxaylyl group, a benzoimidazolyl group, or the like.

The substituted or unsubstituted alkylene group of $L_1$, $L_2$ and $L_3$ may include, e.g., a methylene group, an ethylene group, an n-propylene group, an n-butylene group, an n-hexylene group, an n-heptylene group, an n-octylene group, an n-dodecylene group, or the like.

The substituted or unsubstituted aralkylene group of $L_1$, $L_2$ and $L_3$ may be represented by, e.g., —(CH$_2$)$_x$—Ar', —Ar'—(CH$_2$)$_x$—, or —(CH$_2$)$_x$—Ar'—(CH$_2$)$_y$—. Ar' may represent an arylene group having 6 to 18 ring carbon atoms, e.g., a phenylene group or a naphthylene group, and each of x and y may be an integer of 1 to 24. Total carbon numbers of the arylene group represented using x, y and Ar' may be 7 to 20, e.g., 7 to 14.

The substituted or unsubstituted arylene group of $L_1$, $L_2$ and $L_3$ may include, e.g., a phenylene group, a biphenylene group, a terphenylene group, a naphthylene group, an anthracenylene group, a fluorenyl group, a triphenylene group, or the like. In an implementation, $L_1$, $L_2$ and/or $L_3$ may include, e.g., the substituted or unsubstituted phenylene group.

The substituted or unsubstituted heteroarylene group of $L_1$, $L_2$ and $L_3$ may include, e.g., a pyridylene group, a dibenzoperylene group, a dibenzoethylylene group, or the like.

The substituted or unsubstituted silyl group of $L_1$, $L_2$ and $L_3$ may include, e.g., a dimethylsilylene group or a diphenylsilylene group.

As described above, the organic EL material according to an embodiment may include or introduces a dibenzothiophene part at a meta position of a phenylene group (relative to a bound amine-containing moiety), having a small substituent effect, combined with the nitrogen atom (N) of amine directly or via $L_1$, thereby inducing polarity in a molecule due to a sulfur atom in the dibenzothiophene and improving the amorphous properties of the organic EL material and charge mobility. Therefore, high emission efficiency may be realized while maintaining the properties of the amine improving life. In addition, the dibenzothiophene part may be included at the meta position of the phenylene group combined with the nitrogen atom (N) of the amine directly or via $L_1$, the glass transition temperature of the organic EL material may increase, and the heat resistance and the tolerance of the material may be improved, thereby realizing the long life of the organic EL device.

In an implementation, in the organic EL material of Formula 1, $Ar_1$ and $Ar_2$ may each independently be or include a substituted or unsubstituted phenyl group, and $L_1$, $L_2$ and $L_3$ may each independently be or include a substituted or unsubstituted phenylene group. In an implementation, the organic EL material according to an embodiment may be represented by the following Formula 2.

[Formula 2]

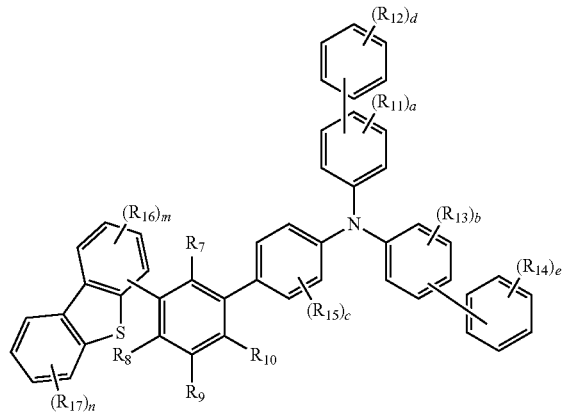

In Formula 2, $R_7$, $R_8$, $R_9$, $R_{10}$, $R_{11}$, $R_{12}$, $R_{13}$, $R_{14}$, $R_{15}$, $R_{16}$ and $R_{17}$ may each independently be or include, e.g., a substituted or unsubstituted aryl group having 6 to 30 ring carbon atoms, a substituted or unsubstituted heteroaryl group having 1 to 30 ring carbon atoms, an alkyl group having 1 to 15 carbon atoms, a silyl group, a halogen atom, a hydrogen atom, or a deuterium atom. In addition, a, b and c may each independently be an integer of 0 to 4, d and e may each independently be an integer of 0 to 5, m may be an integer of 0 to 3, and n may be an integer of 0 to 4.

In Formula 2, the substituted or unsubstituted aryl group having 6 to 30 ring carbon atoms, the substituted or unsubstituted heteroaryl group having 1 to 30 ring carbon atoms, the alkyl group having 1 to 15 carbon atoms, the silyl group, and the halogen atom of $R_7$, $R_8$, $R_9$, $R_{10}$, $R_{11}$, $R_{12}$, $R_{13}$, $R_{14}$, $R_{15}$, $R_{16}$ and $R_{17}$ may be the same substituted or unsubstituted aryl group having 6 to 30 ring carbon atoms, substituted or unsubstituted heteroaryl group having 1 to 30 ring carbon atoms, alkyl group having 1 to 15 carbon atoms, substituted or unsubstituted silyl group, and halogen atom of $R_1$, $R_2$, $R_3$, $R_4$, $R_5$ and $R_6$ in Formula 1.

In an implementation, neighboring ones of $R_8$-$R_{14}$ in Formula 2 may combine to each other to form a saturated or unsaturated ring.

In the material represented by Formula 1, $Ar_1$ and $Ar_2$ may each independently be or include a substituted or unsubstituted phenyl group, and $L_1$, $L_2$ and $L_3$ may each independently be or include a substituted or unsubstituted phenylene group, thereby securing the conjugation of amine and improving the charge tolerance of the material.

In an implementation, carbon at the meta position of a second phenylene group combined with the nitrogen atom (N) of amine via a first phenylene group may be combined with carbon at position 4 of dibenzothiophene. In an implementation, the organic EL material may be represented by the following Formula 3.

[Formula 3]

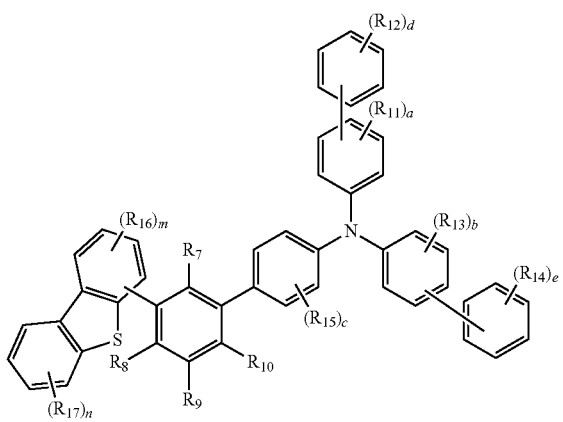

In the organic EL material represented by Formula 2, carbon at the meta position of a second phenylene group combined with the nitrogen atom (N) of amine via a first phenylene group may be combined with carbon at position 4 of dibenzothiophene, thereby breaking molecular planarity and improving amorphous properties of the material.

In an implementation, the organic EL material may include one of the following Compounds 1 to 96.

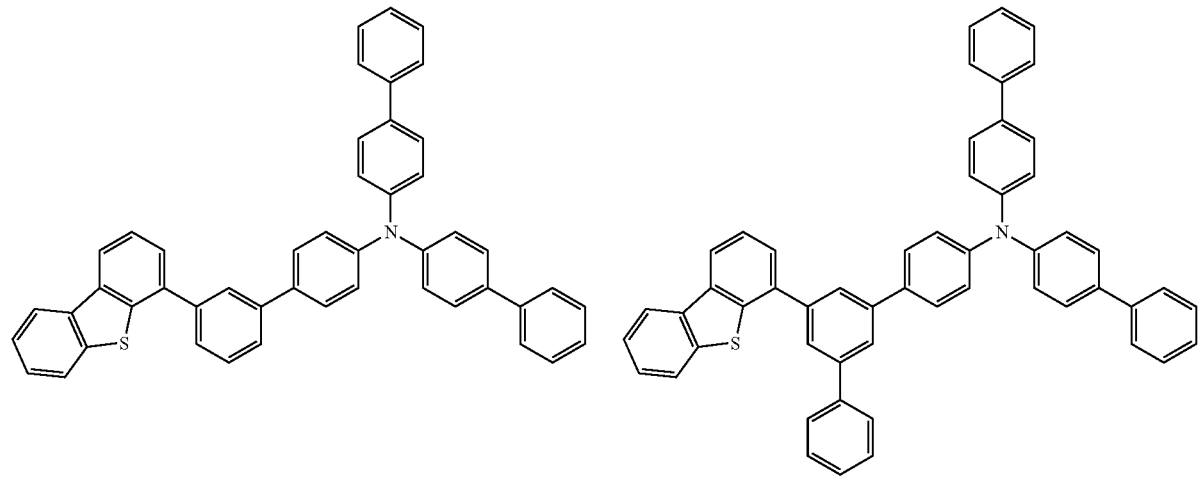

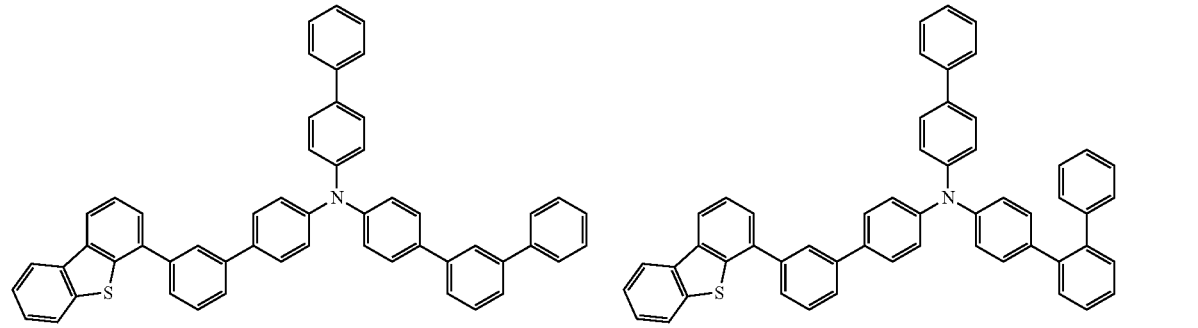

-continued
5
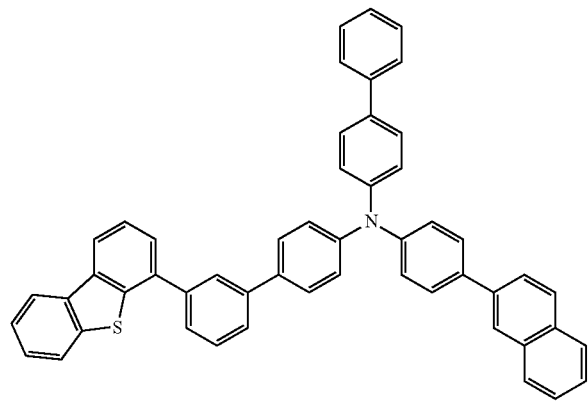
6
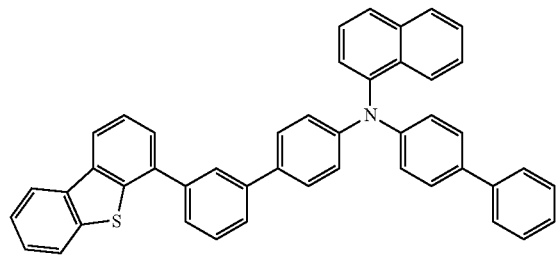
7
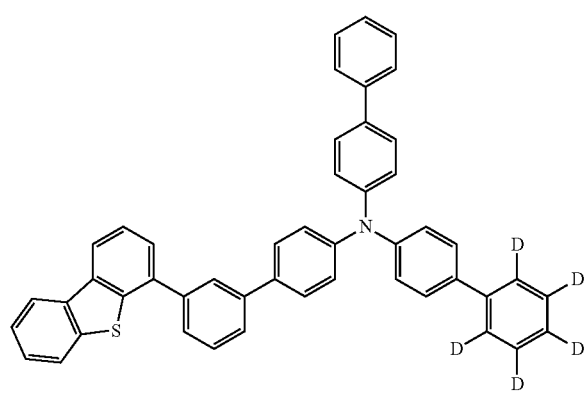
8
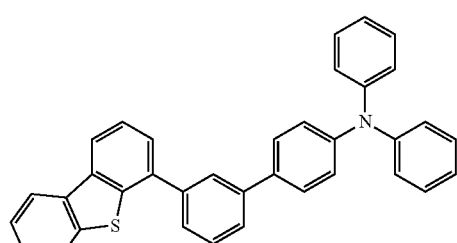
9
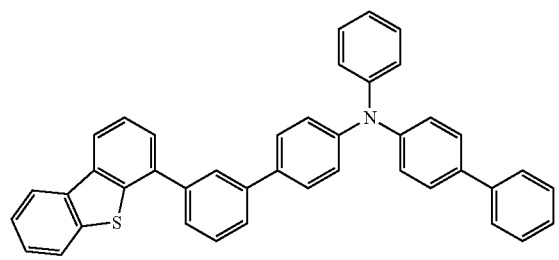
10
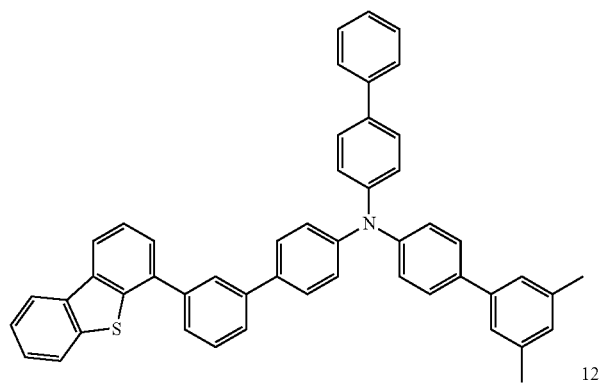
11
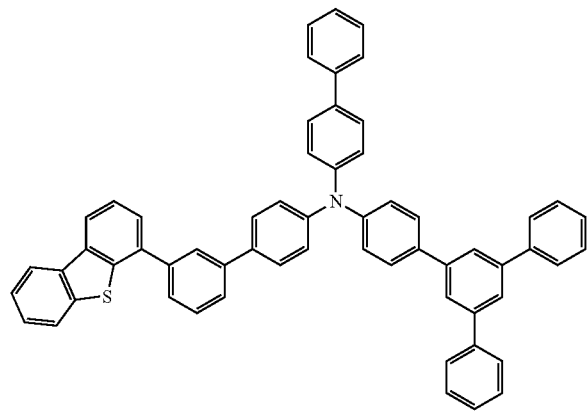
12
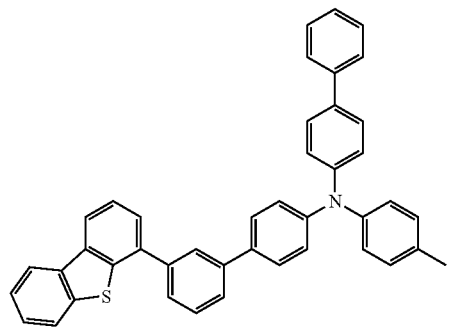

-continued
13
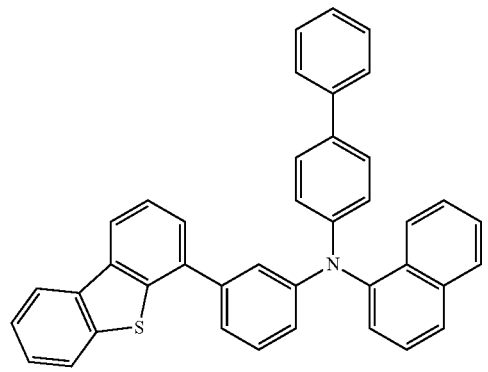
14
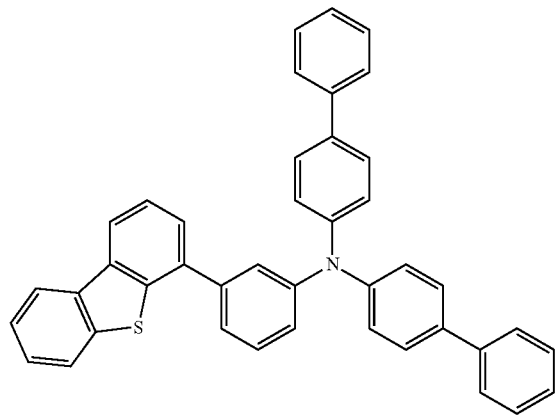
15
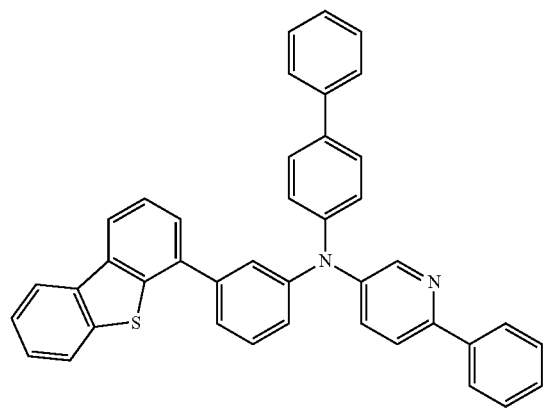
16
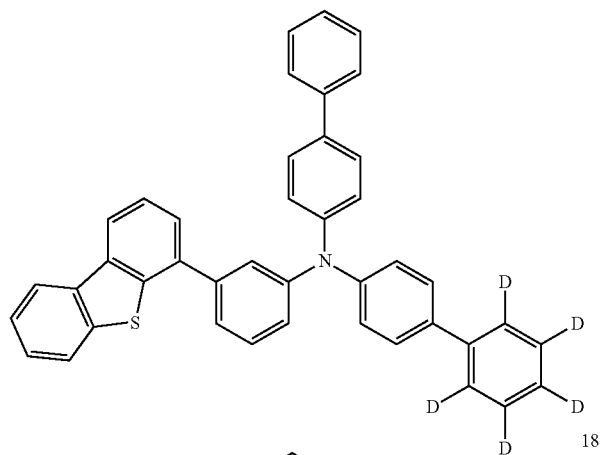
17
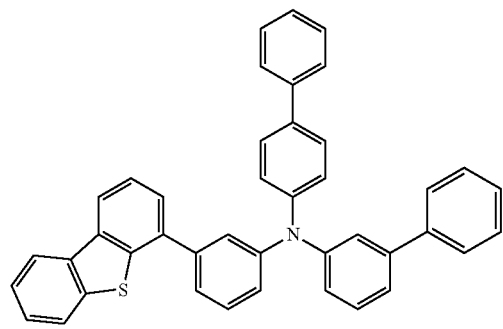
18
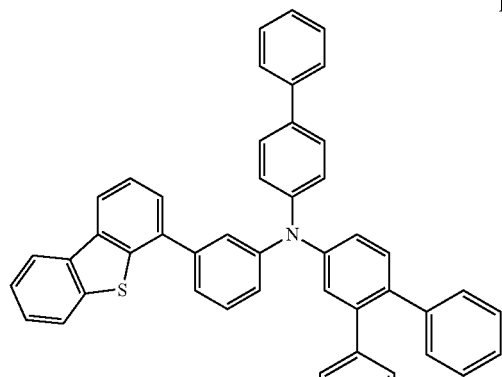
19
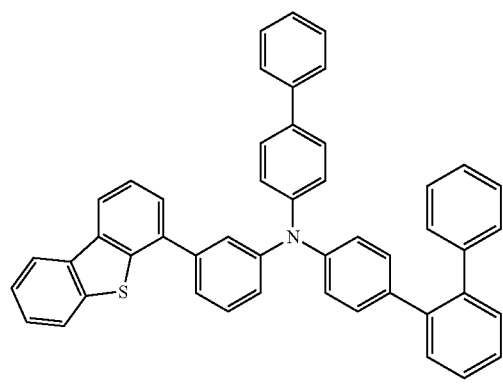
20
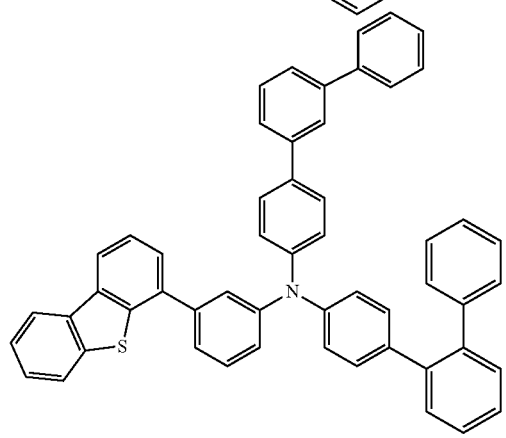

-continued
21
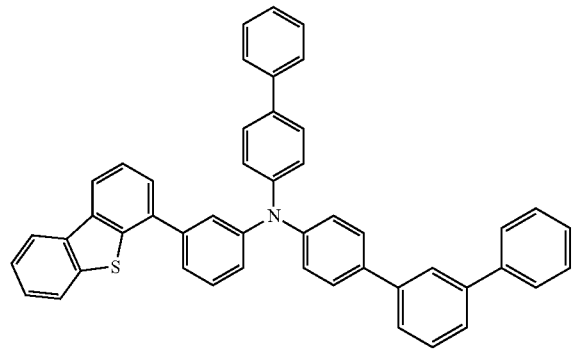
22
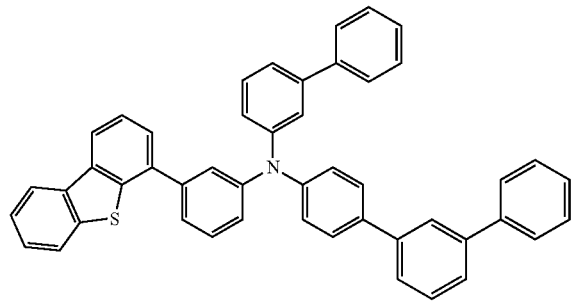
23
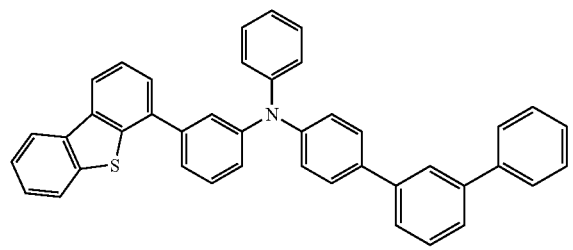
24
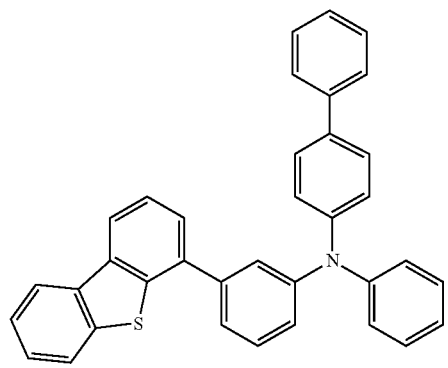
25
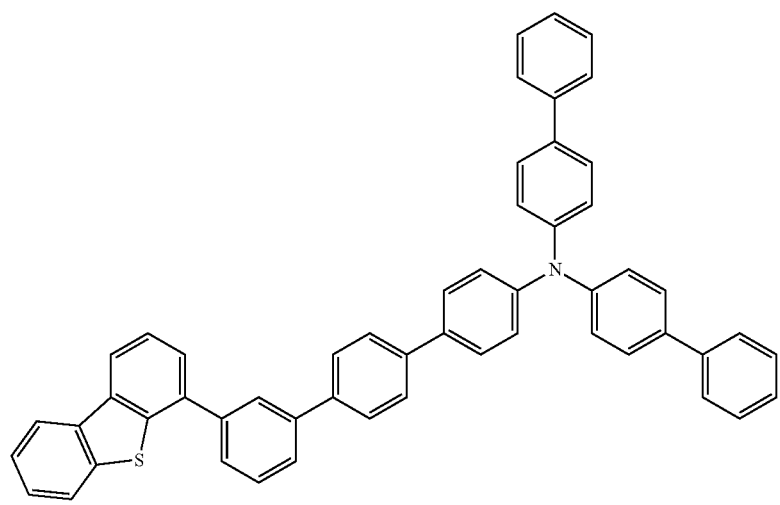

26
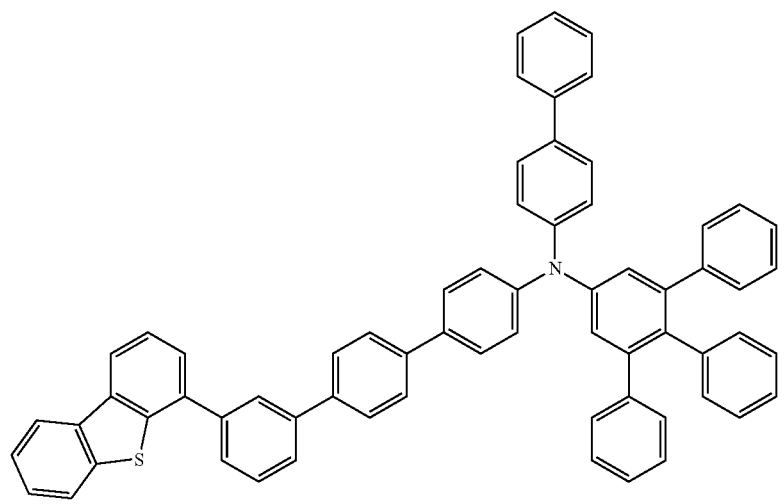
27
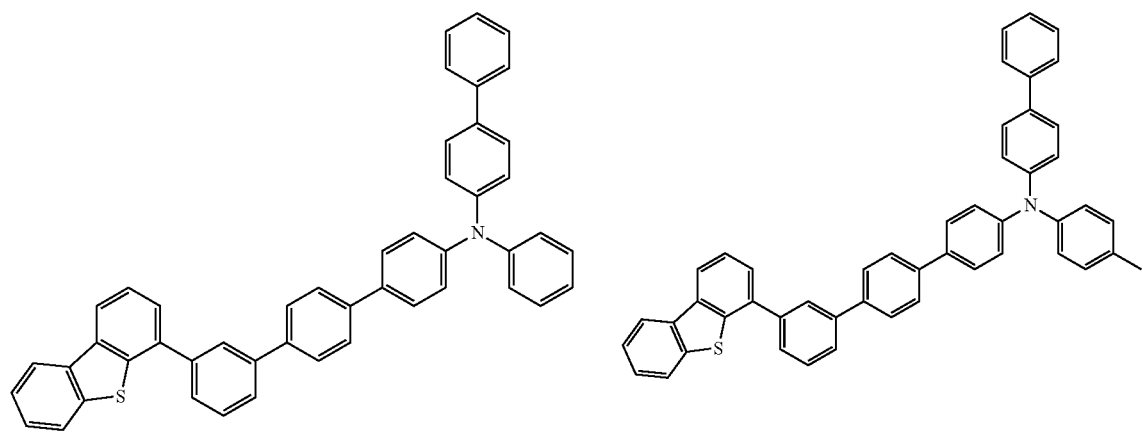
28
29
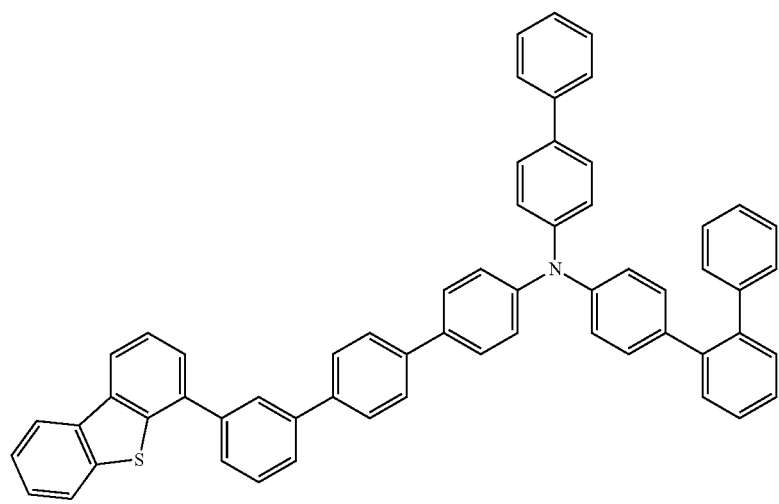

-continued
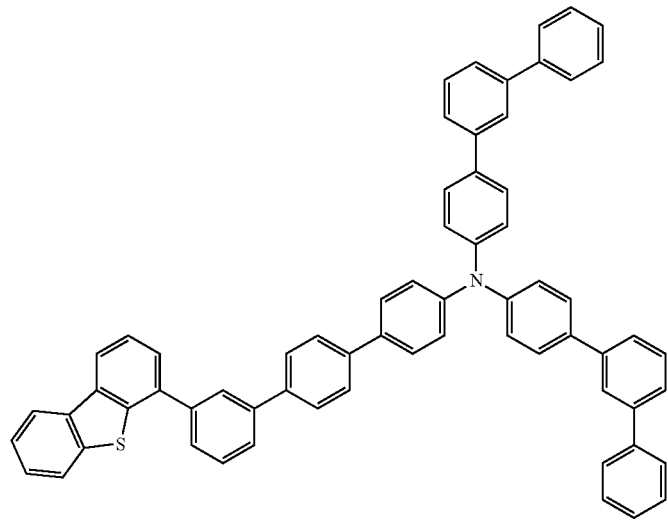
30
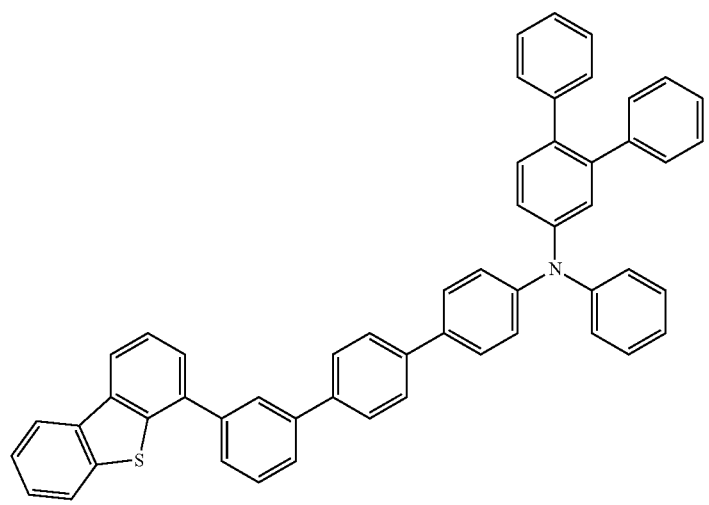
31
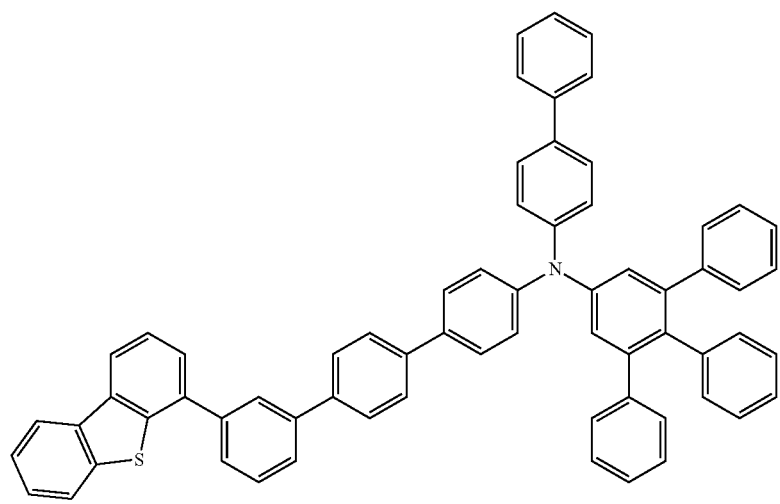
32

-continued
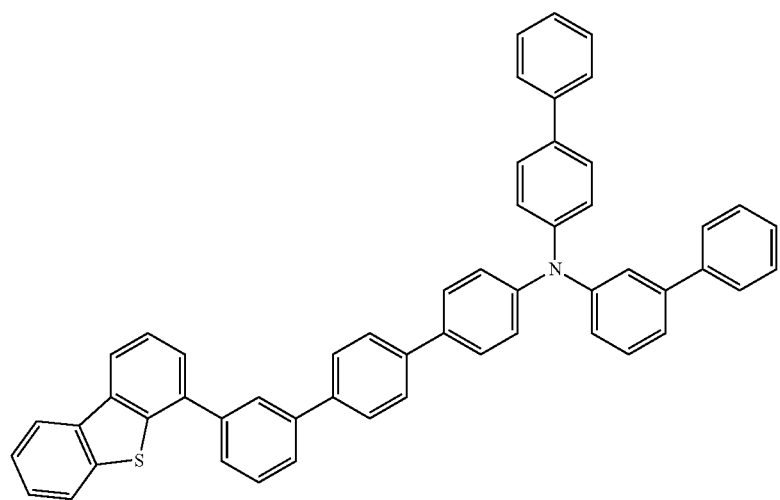
33
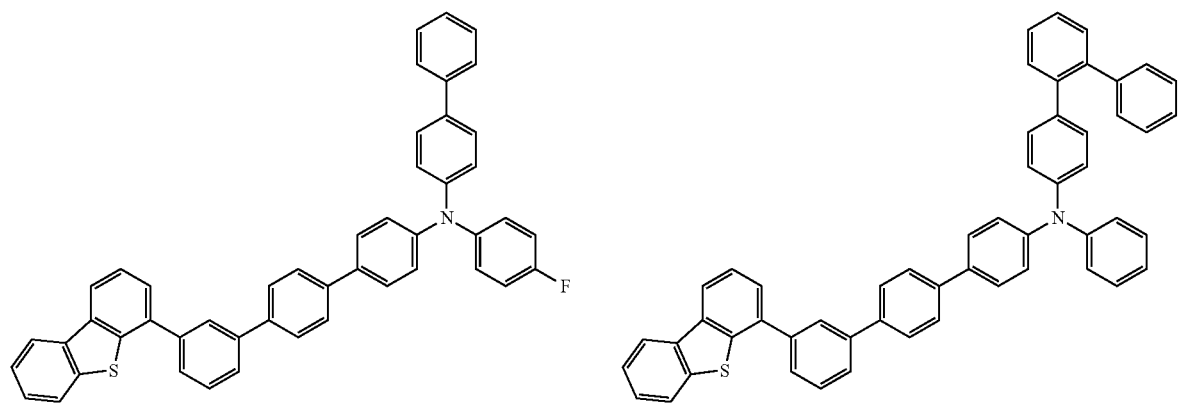
34  35
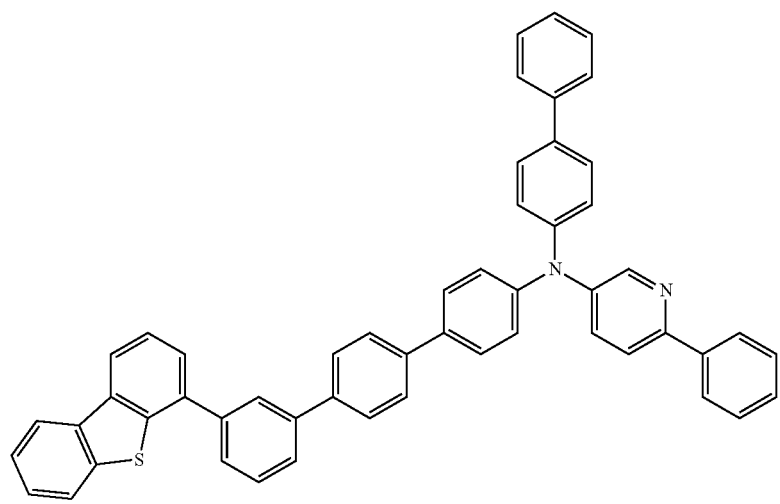
36

37
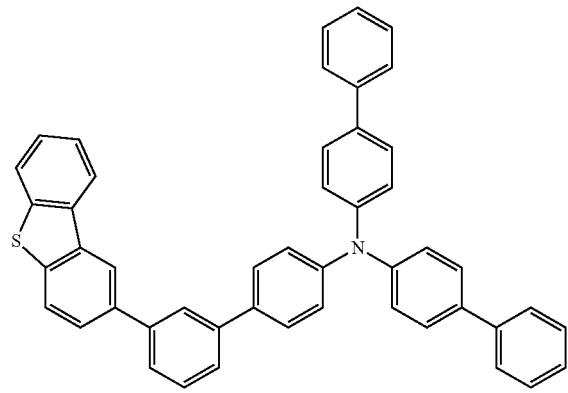
38
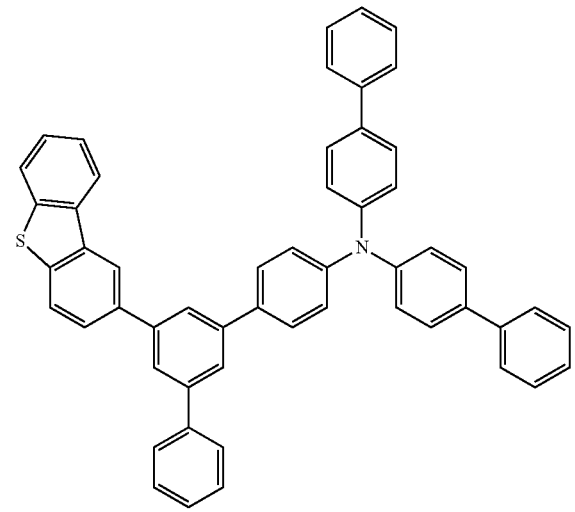
39
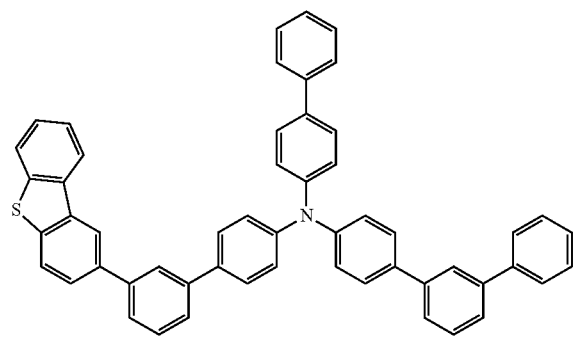
40
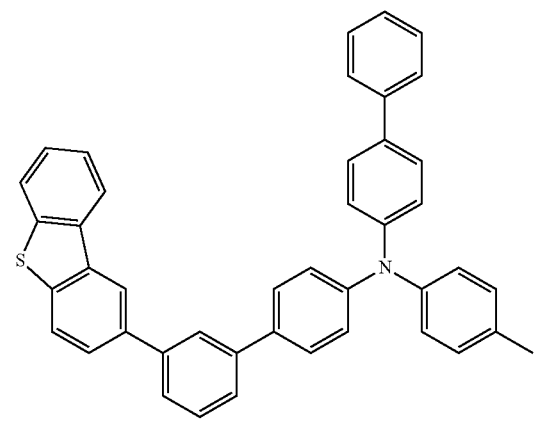
41
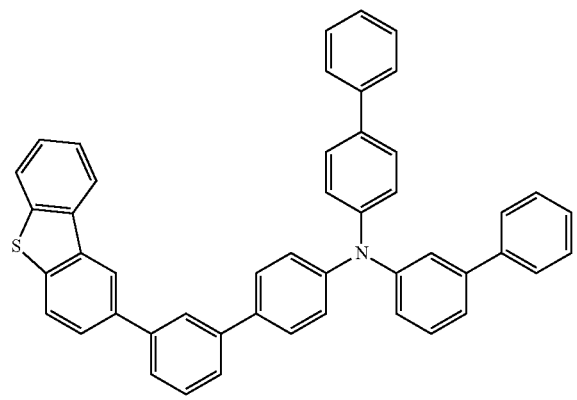
42
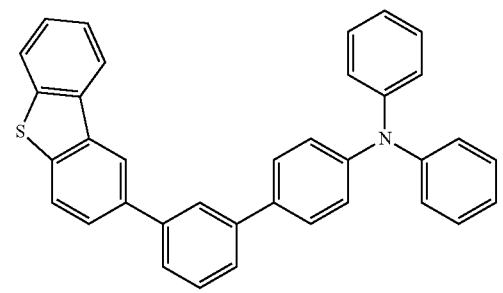

-continued
43
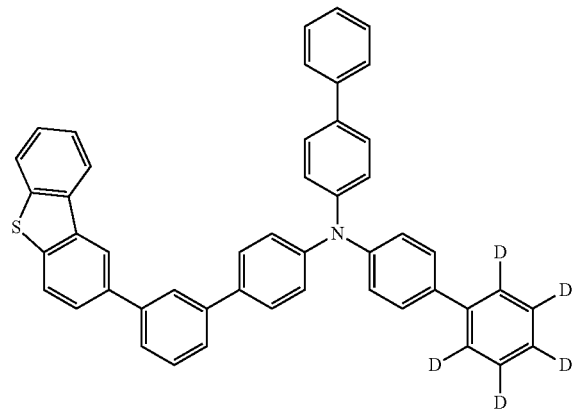
44
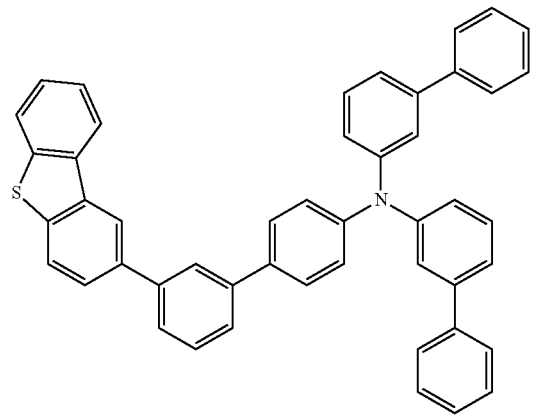
45
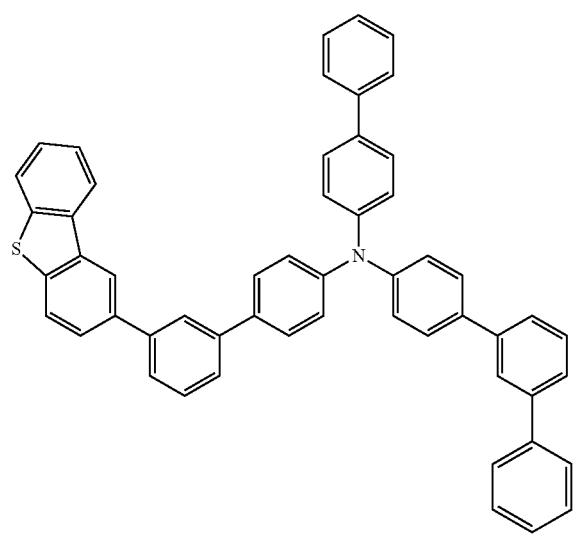
46
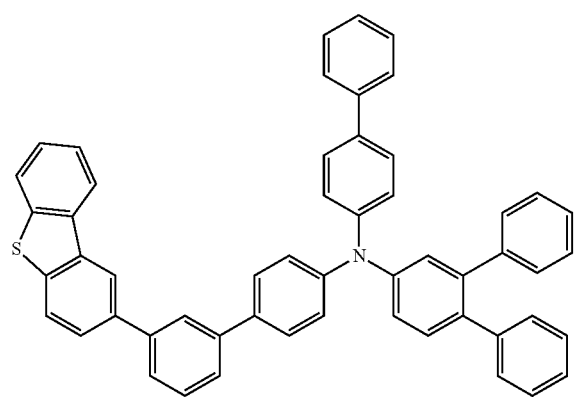
47
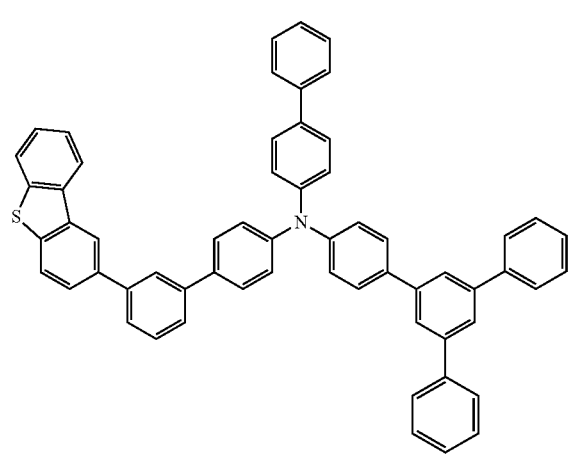
48
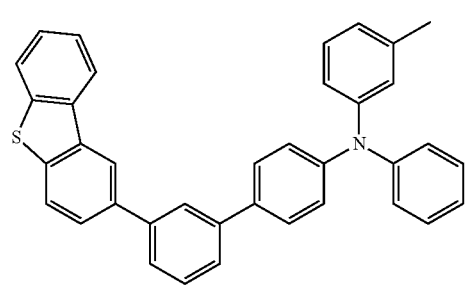

-continued
49
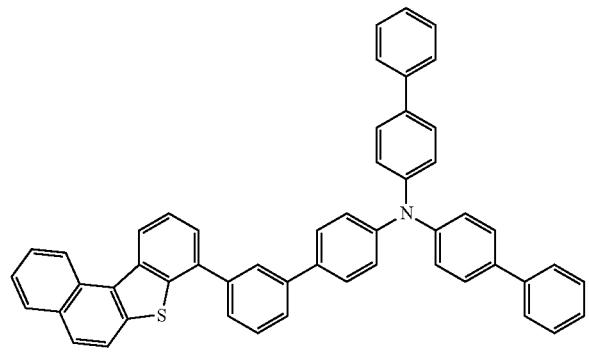
50
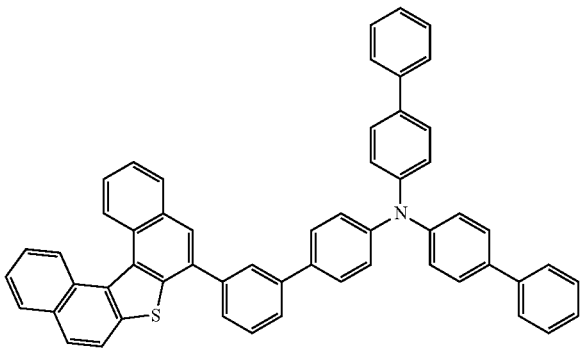
51
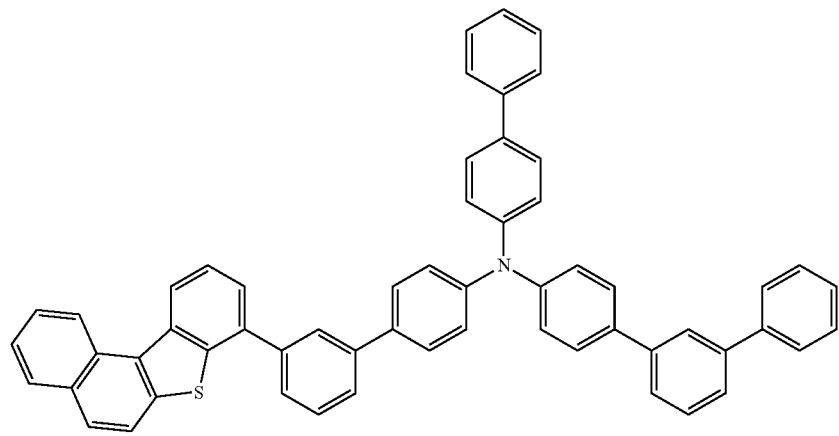
52
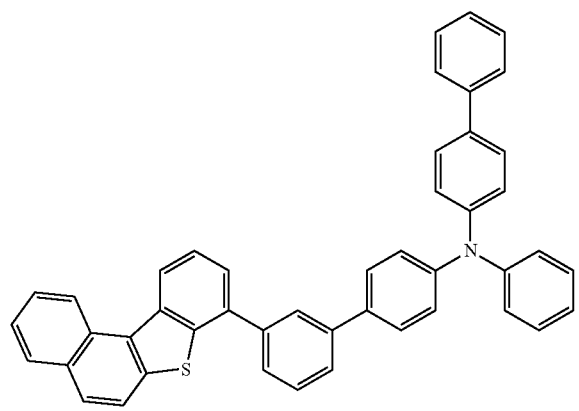
53
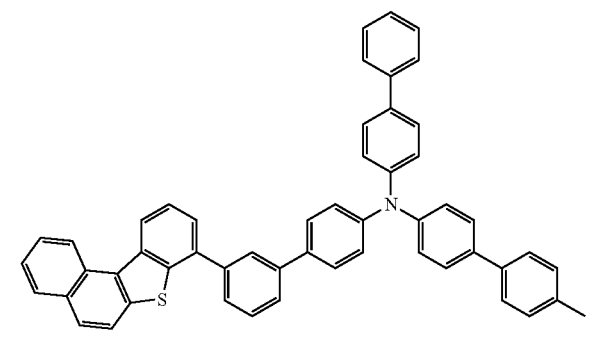
54
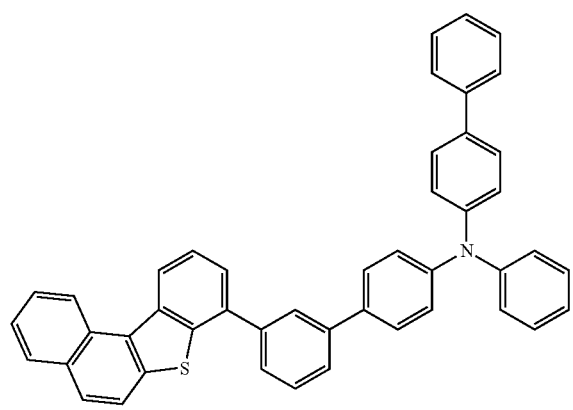
55
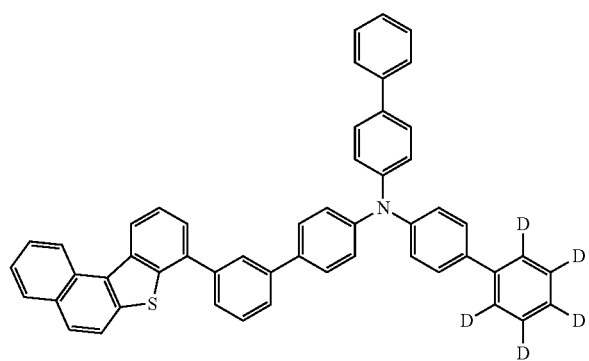

56
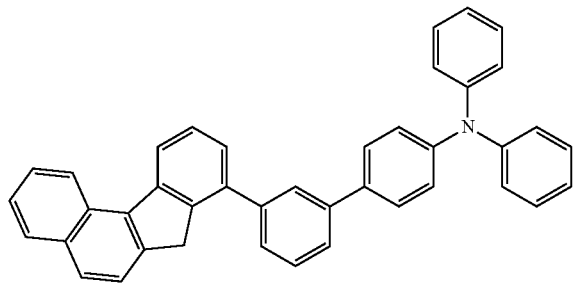
57
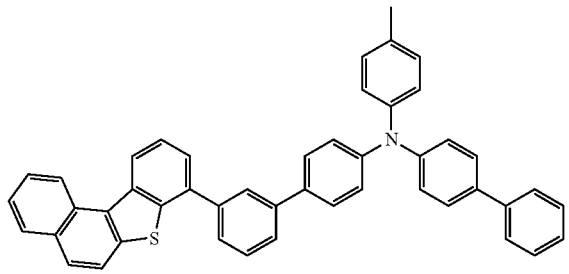
58
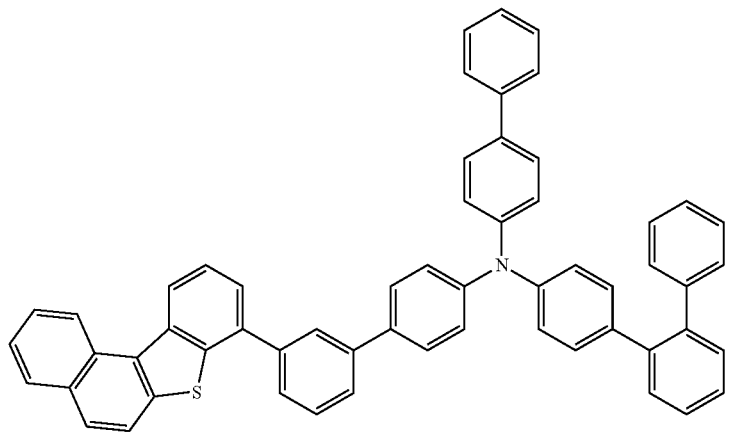
59
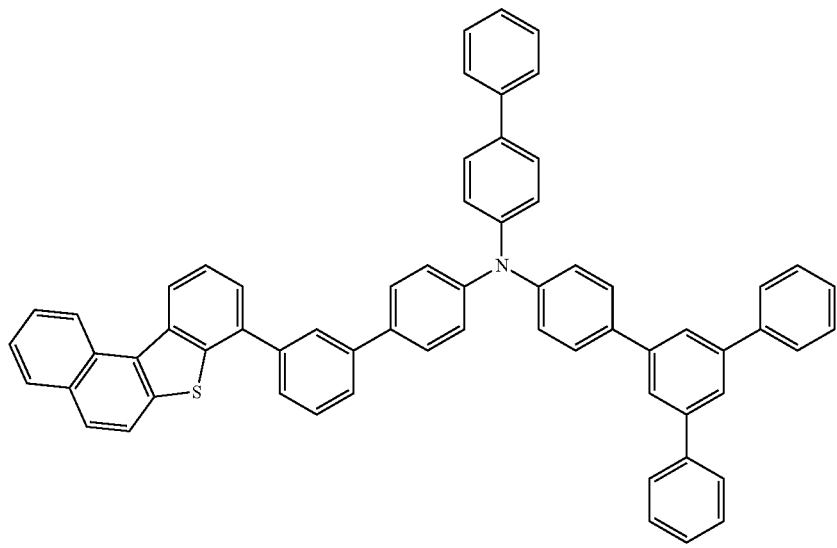

-continued
60
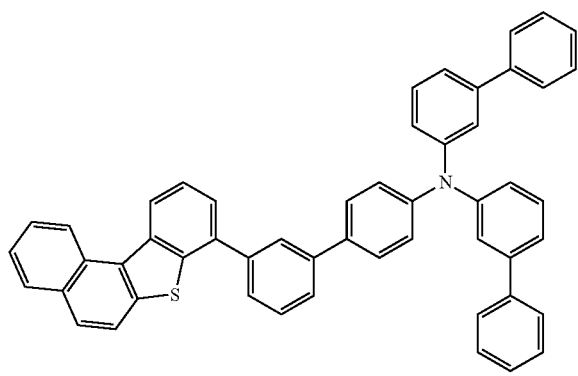
61
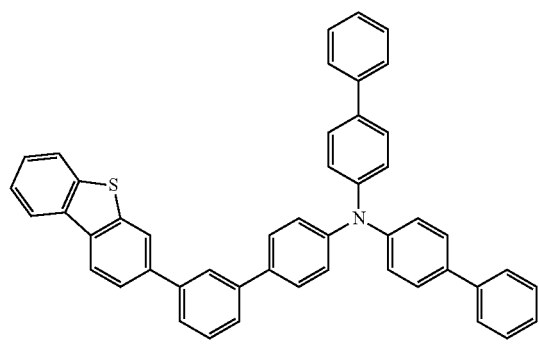
62
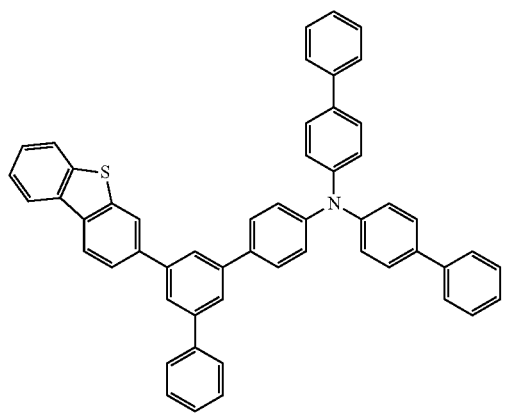
63
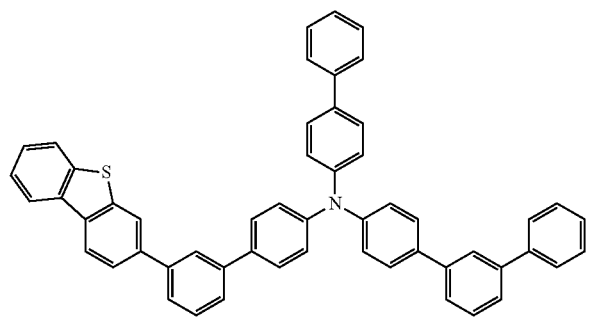
64
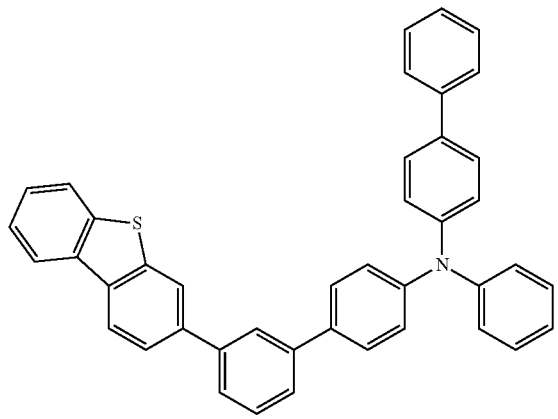
65
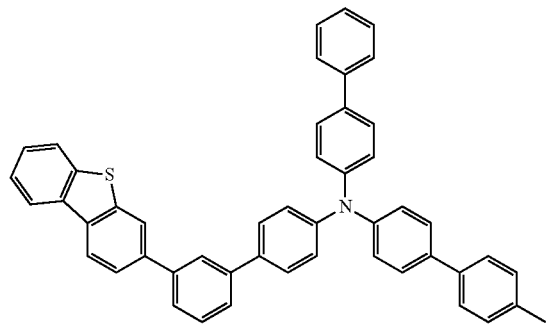
66
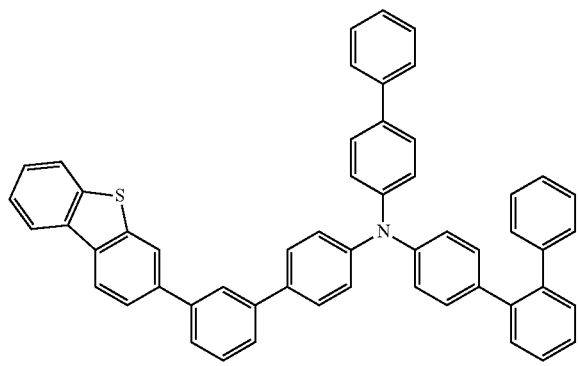
67
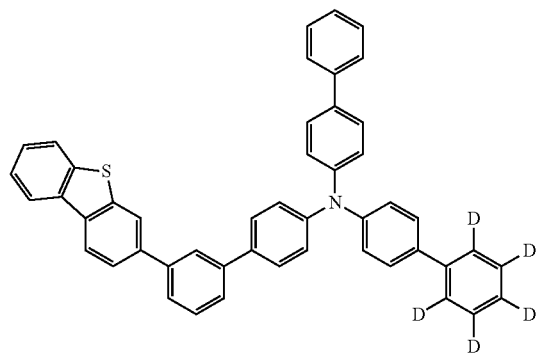

68
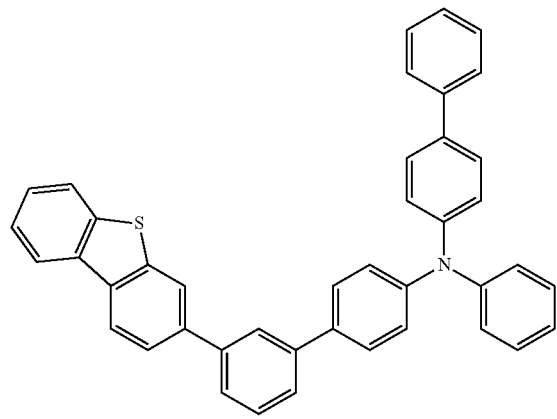
69
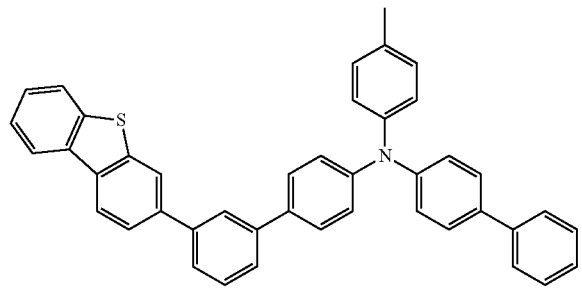
70
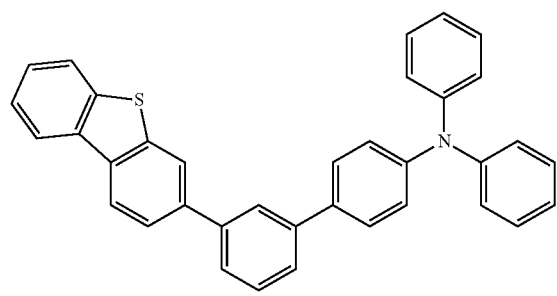
71
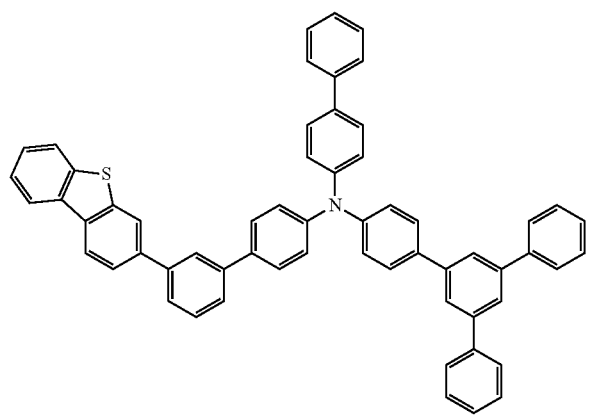
72
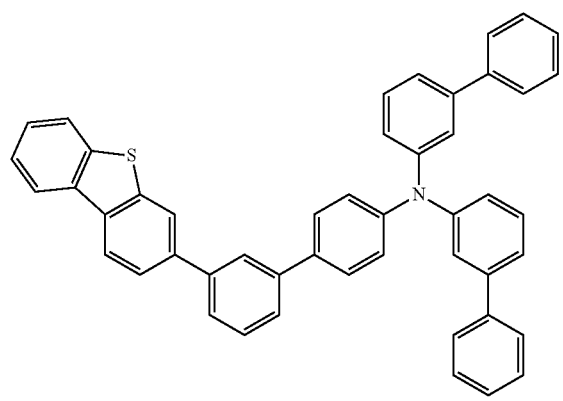
73
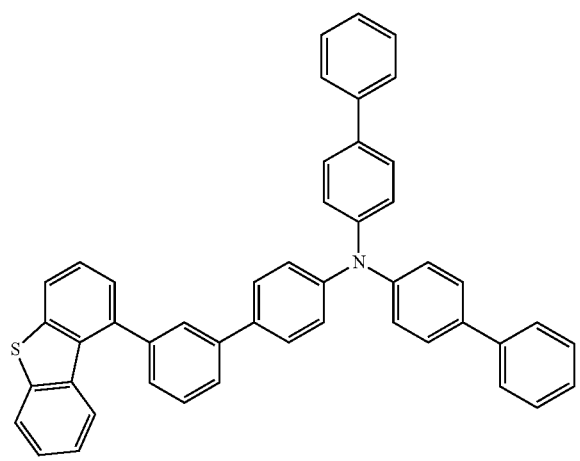

-continued
74
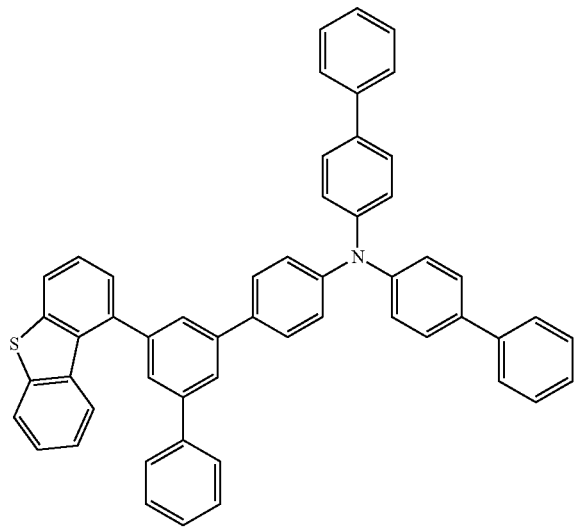
75
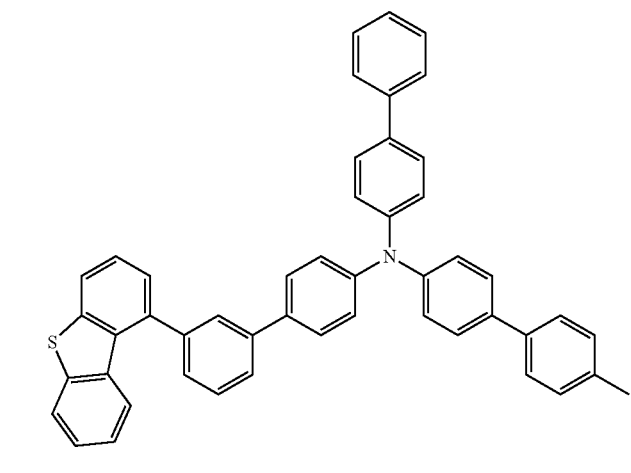
76
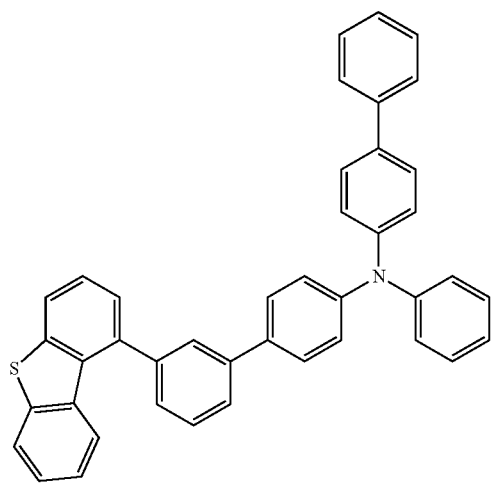
77
78
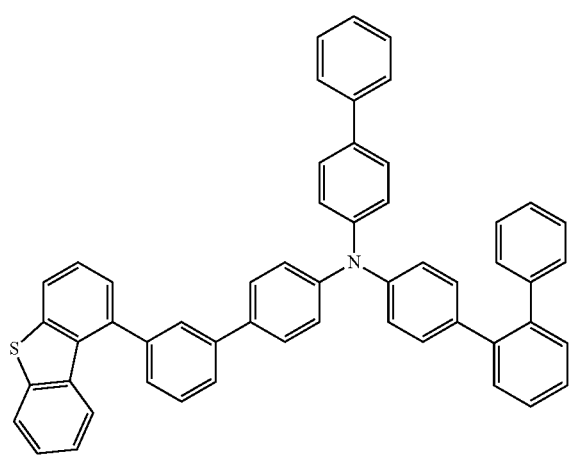
79
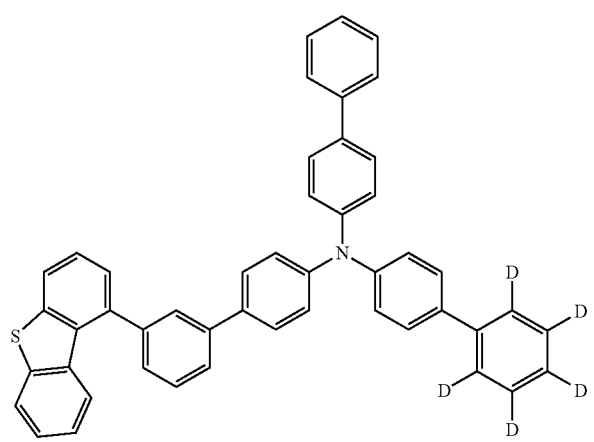

80
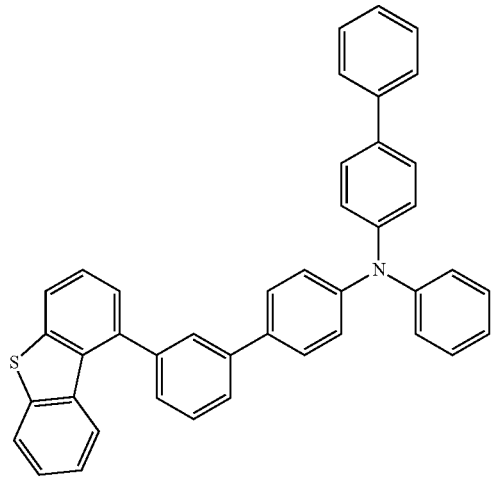
81
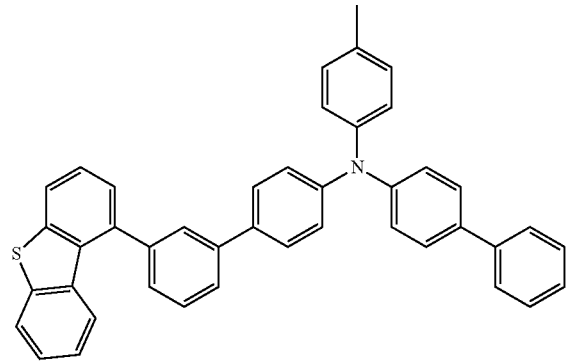
82
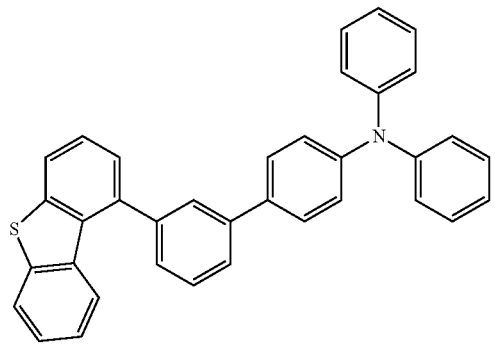
83
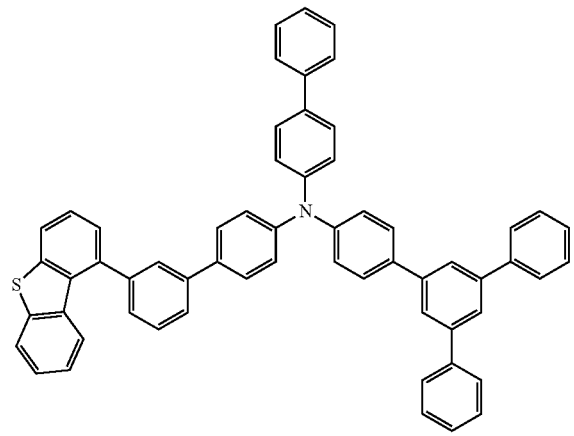
84
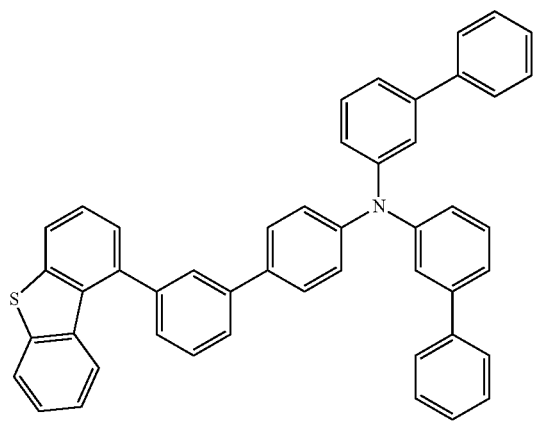
85
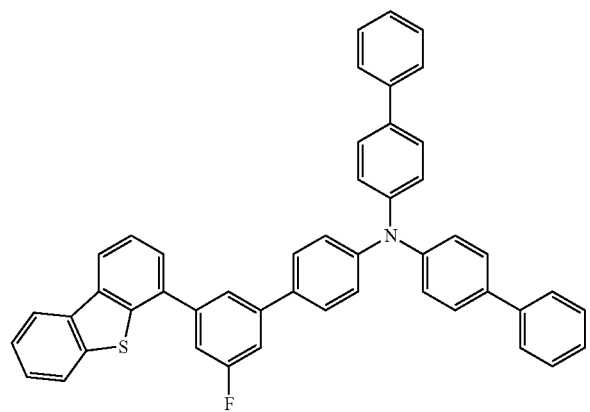

-continued
86
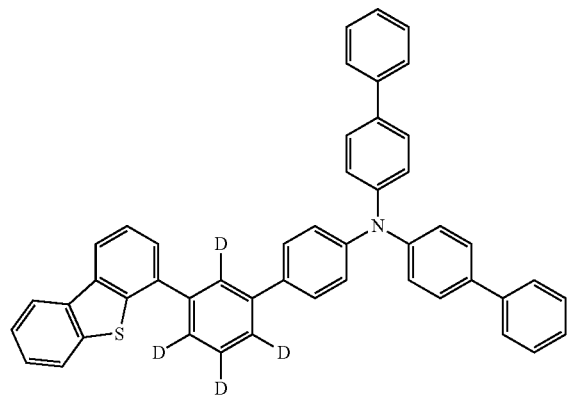
87
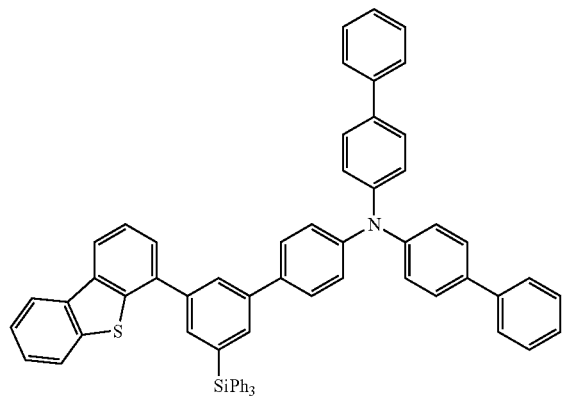
88
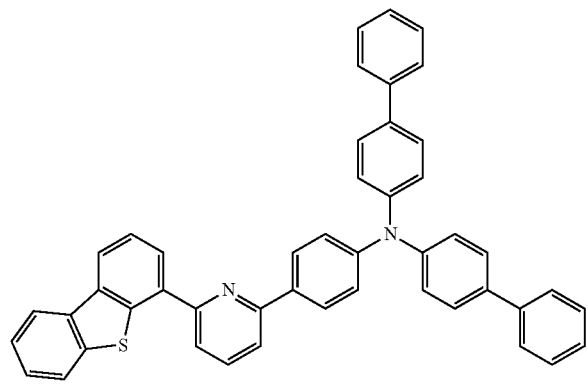
89
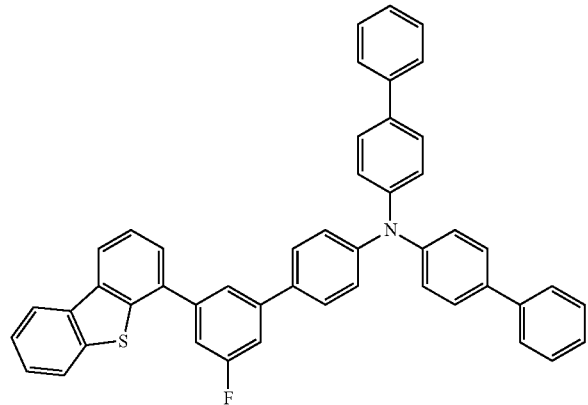
90
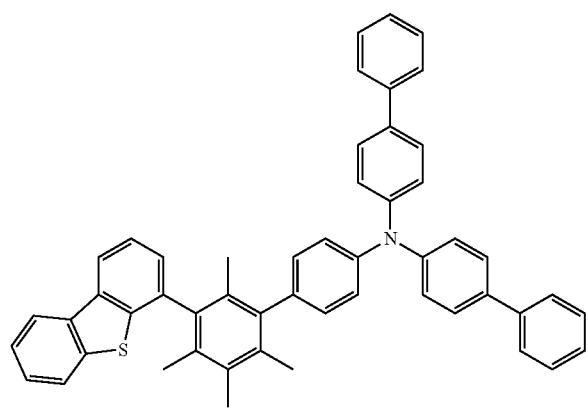
91
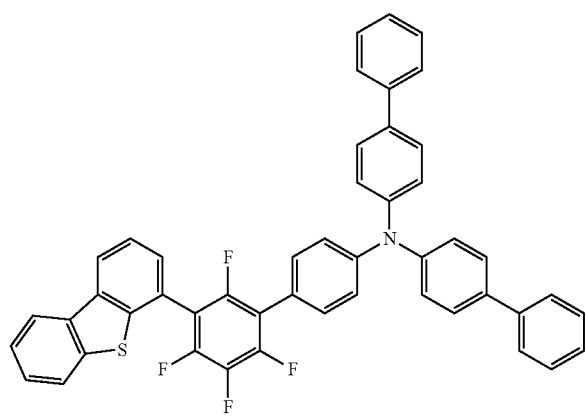

-continued

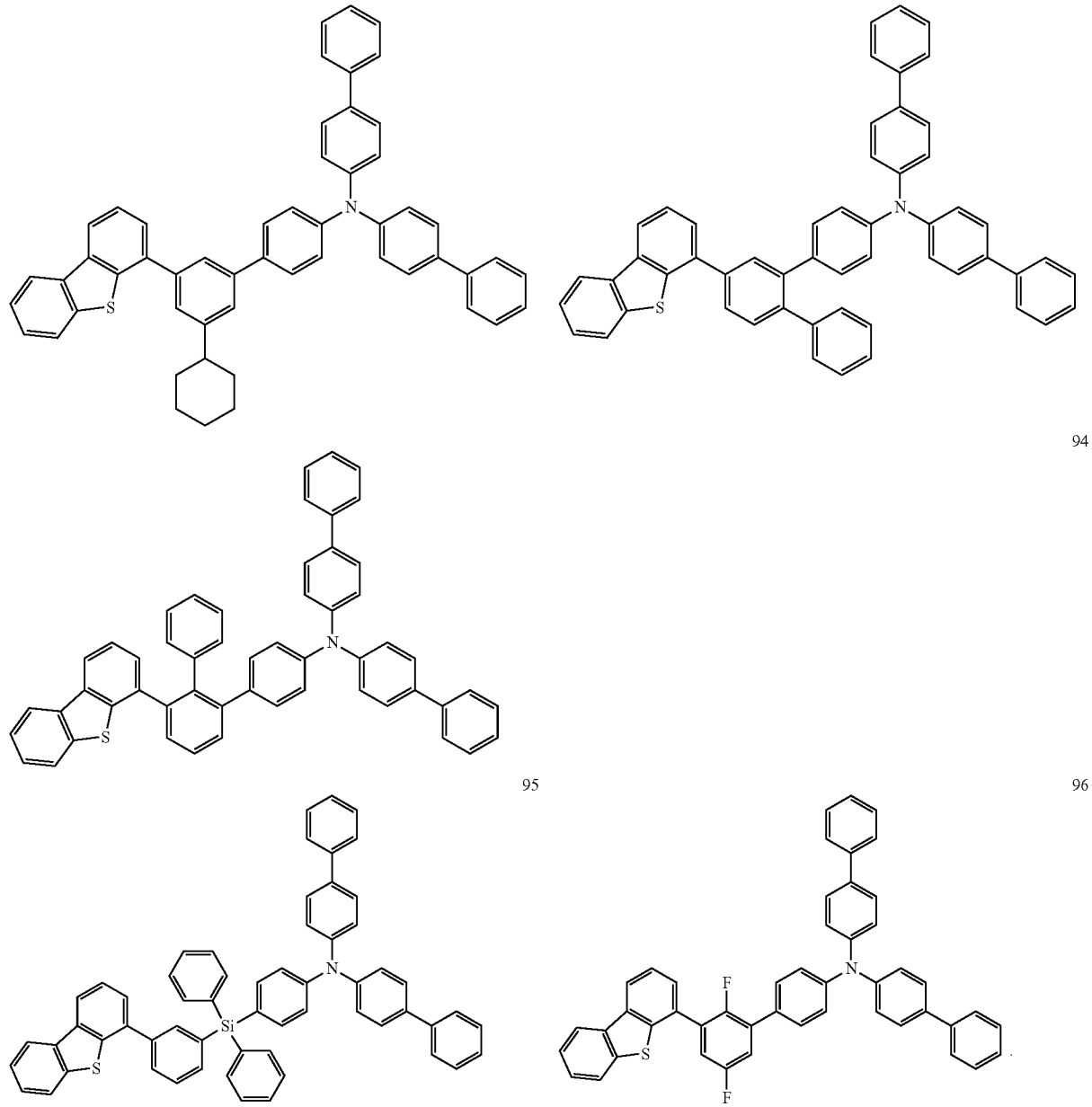

The organic EL material according to an embodiment may be used or included in at least one layer of stacking layers between an emission layer and an anode in an organic EL device. Accordingly, the amorphous properties of the material may be improved, and charge mobility may be increased, thereby realizing the long life and the high efficiency of the organic EL device. In addition, the glass transition temperature may increase, heat-resistance and tolerance may be improved, and the increase of the life of the organic EL device may be realized.

(Organic EL Device)

The organic EL device using the organic EL material according to an embodiment. FIG. 1 illustrates a schematic diagram of the organic EL device 100 according to an embodiment. The organic EL device 100 may be provided with or include, e.g., a substrate 102, an anode 104, a hole injection layer 106, a hole transport layer 108, an emission layer 110, an electron transport layer 112, an electron injection layer 114, and a cathode 116. In an implementation, the organic EL material may be included in a layer of (e.g., one of) stacking layers between the emission layer and the anode.

A case that the organic EL material according to an embodiment is used in the hole transport layer 108 will be explained.

The substrate 102 may be e.g., a transparent glass substrate, a semiconductor substrate formed using silicon, or the like, a flexible substrate of a resin, or the like.

The anode 104 may be disposed on the substrate 102 and may be formed using, e.g., indium tin oxide (ITO), indium zinc oxide (IZO), or the like.

The hole injection layer (HIL) 106 may be disposed on the anode 104 and may be formed using a suitable material and to a thickness of about 10 nm to 150 nm. For example, the HIL may include triphenylamine-containing polyether ketone (TPAPEK), 4-isopropyl-4'-methyldiphenyliodoniumtetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), 4,4',4''-tris{N,N-diphenylamino}triphenylamine (TDATA), 4,4',4''-tris(N,N-2-naphthylphenylamino)triphenylamine (2-NATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate (PANI/PSS), or the like.

The hole transport layer (HTL) 108 may be formed on the hole injection layer 106 using the organic EL material according to an embodiment and to a thickness of about 10 nm to 150 nm. The hole transport layer 108 including the organic EL material according to an embodiment may be formed by, e.g., a vacuum evaporation method.

The emission layer (EL) 110 may be formed on the hole transport layer 108 using a suitable host material and to a thickness of about 10 nm to 60 nm. The host material used in the emission layer 110 may include, e.g., tris(8-quinolinolato)aluminum (Alq3), 4,4'-N,N'-dicarbazole-biphenyl (CBP), poly(n-vinylcarbazole) (PVK), 9,10-di(naphthalene-2-yl)anthracene (ADN), 4,4',4''-tris(N-carbazolyl)triphenylamine (TCTA), 1,3,5-tris(N-phenylbenzimidazole-2-yl)benzene (TPBI), 3-tert-butyl-9,10-di(naphtho-2-yl)anthracene (TBADN), distyrylarylene (DSA), 4,4'-bis(9-carbazole)-2,2'-dimethyl-biphenyl (dmCBP), or the like.

The emission layer 110 may include a dopant material, e.g., styryl derivatives (for example, 1,4-bis[2-(3-N-ethylcarbazoryl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalene-2-yl)vinyl)phenyl-N-phenylbenzenamine (N-BDAVBi)), perylene and the derivatives thereof (for example, 2,5,8,11-tetra-t-butylperylene (TBPe)), pyrene and the derivatives thereof (for example, 1,1-dipyrene, 1,4-dipyrenylbenzene, 1,4-bis(N,N-diphenylamino)pyrene), or the like.

The electron transport layer (ETL) 112 may be formed on the emission layer 110 and to a thickness of about 15 nm to 50 nm using a material including, e.g., tris(8-hydroxyquinolinato)aluminum (Alq3) or a nitrogen-containing aromatic ring (for example, a material including a pyridine ring such as 1,3,5-tri[(3-pyridyl)-phen-3-yl]benzene, a material including a triazine ring such as 2,4,6-tris(3'-(pyridine-3-yl)biphenyl-3-yl)1,3,5-triazine, or a material including an imidazole derivative such as 2-(4-N-phenylbenzoimidazolyl-1-ylphenyl)-9,10-dinaphthylanthracene).

The electron injection layer (EIL) 114 may be formed on the electron transport layer 112 and to a thickness of about 0.3 nm to 9 nm using, e.g., a material including lithium fluoride (LiF), lithium-8-quinolinato (Liq), etc.

The cathode 116 may be disposed on the electron injection layer 114 and may be formed using, e.g., a metal such as aluminum (Al), silver (Ag), lithium (Li), magnesium (Mg), calcium (Ca), a mixture thereof, or a transparent material such as ITO and IZO.

Each electrode and each layer forming the organic EL device according to an embodiment may be formed by selecting an appropriate layer forming method according to materials including a vacuum evaporation method, a sputtering method, various coating methods, etc. In addition, the hole transport layer 108 formed using the organic EL material according to an embodiment may be formed by a vacuum evaporation method, as described above.

In the organic EL device 100 according to an embodiment, a hole transport layer realizing long life and high efficiency may be formed using the organic EL material described above.

In the organic EL device 100 according to an embodiment, the organic EL material may be used as a material of a hole injection layer. As described above, an organic EL device with high efficiency and long life may be realized by using the organic EL material in at least one layer of stacking layers disposed between an emission layer and an anode.

In an implementation, the organic EL material according to an embodiment may be applied in an organic EL display of an active matrix using a TFT.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

PREPARATION METHOD

The above-mentioned organic EL material may be synthesized by e.g., the following method.

(Synthetic Method of Compound 1)

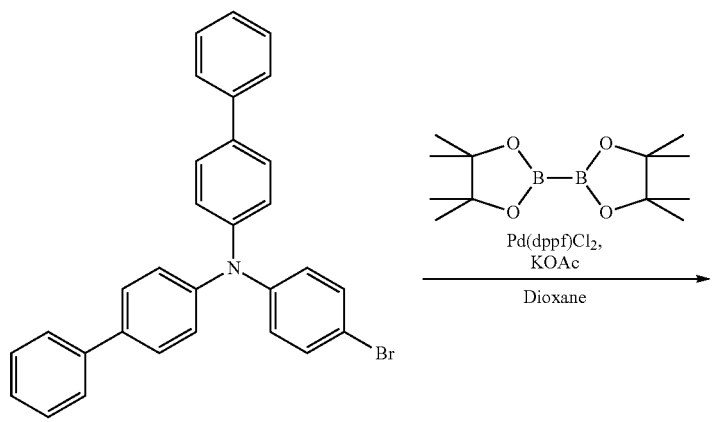

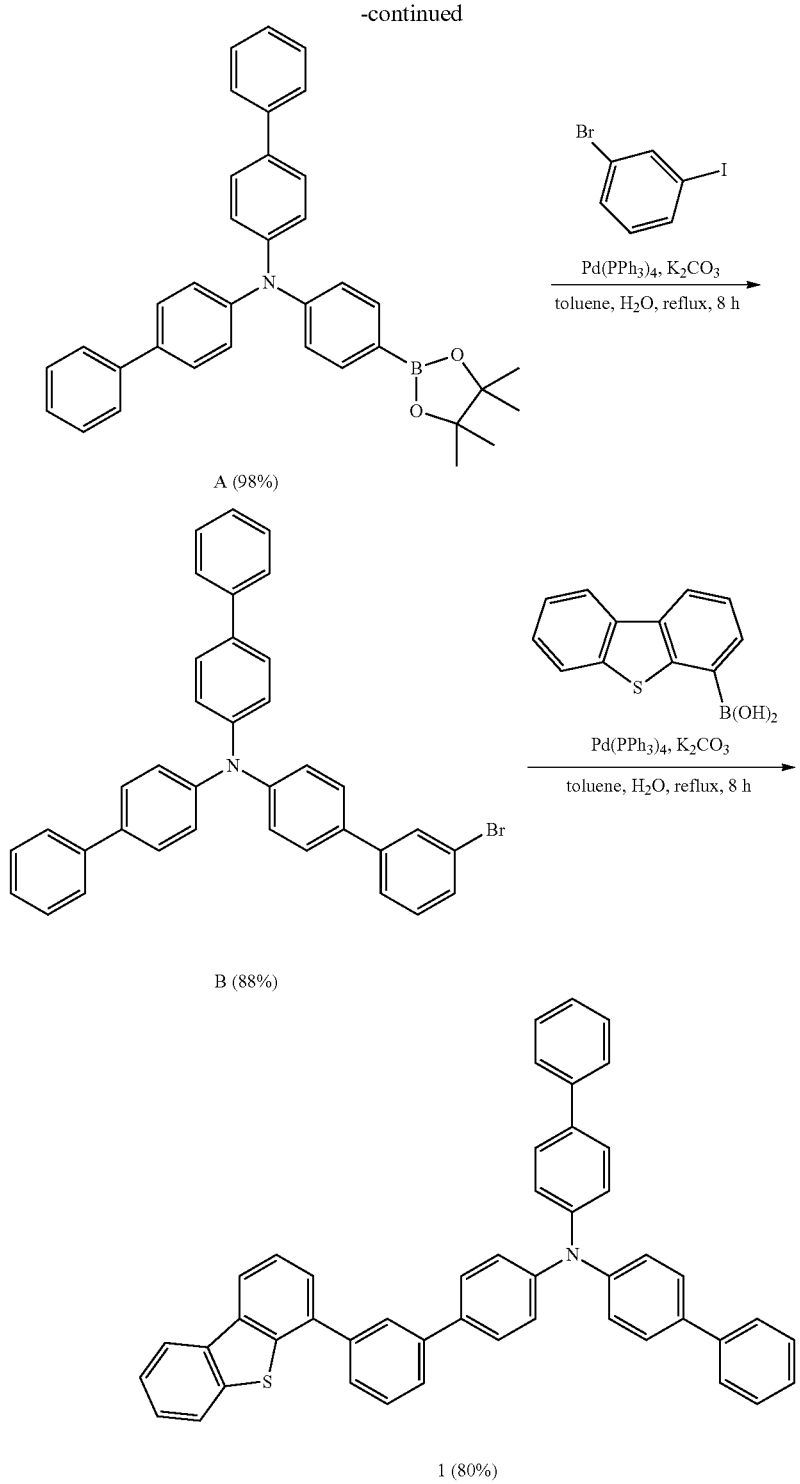

(Synthesis of Compound A)

Under an Ar atmosphere, 53.8 g of N-[1,1'-biphenyl]-4-yl-N-(4-bromophenyl)-[1,1'-biphenyl]-4-amine, 6.46 g of Pd(dppf)Cl$_2$·H$_2$Cl$_2$, 33.3 g of KOAc, and 33.0 g of bis(pinacolato)diboron were added to a 2 L flask, followed by degassing under vacuum in a dioxane solvent and stirring at about 100° C. for about 12 hours. Solvents were distilled, CH$_2$Cl$_2$ and water were added thereto, an organic phase was separated, and magnesium sulfate and activated clay were added. Then, the resultant product was filtered with suction, and solvents were distilled. The crude product thus obtained was separated using silica gel column chromatography (using a mixed solvent of dichloromethane and hexane) to produce 56.8 g of Compound A as a white solid (Yield 98%). The molecular weight of Compound A measured by FAB-MS was 523.

(Synthesis of Compound B)

Under an Ar atmosphere, 10.0 g of Compound A, 6.00 g of 1-iodo-3-bromobenzene, 1.54 g of Pd(PPh$_3$)$_4$, and 5.25 g of potassium carbonate were added to a 300 mL, three-necked flask, followed by heating and stirring in a mixed solvent of 450 mL of toluene and 60 mL of water at about 90° C. for about 8 hours. After air cooling, water was added, an organic layer was separated, and solvents were distilled. The crude product thus obtained was separated using silica gel column chromatography (using a mixed solvent of dichloromethane and hexane) to produce 9.29 g of Compound B as a white solid (Yield 88%). The molecular weight of Compound B measured by FAB-MS was 551.

(Synthesis of Compound 1 in Formula 29)

Under an Ar atmosphere, 3.10 g of Compound B, 1.28 g of dibenzothiophene-4-boronic acid, 0.84 g of Pd(PPh$_3$)$_4$, and 2.35 g of potassium carbonate were added to a 500 mL, three-necked flask, followed by heating and stirring in a mixed solvent of 170 mL of toluene and 80 mL of water at about 90° C. for about 8 hours. After air cooling, water was added, an organic layer was separated, and solvents were distilled. The crude product thus obtained was separated using silica gel column chromatography (using a mixed solvent of dichloromethane and hexane) and recrystallized using a mixed solvent of toluene and hexane to produce 2.94 g of Compound 1 as a white solid (Yield 80%). The molecular weight of Compound 1 measured by FAB-MS was 656. The chemical shift values (δ) of Compound 1 measured by $^1$H-NMR (CDCl$_3$) were 8.46-8.41 (m, 2H), 8.20 (d, 1H, J=7.80 Hz), 7.98 (d, 1H, J=7.90 Hz), 7.58-7.50 (m, 18H), 7.48-7.41 (m, 4H), 6.69-6.65 (m, 4H).

In an implementation, the organic EL material according to another embodiment may be synthesized according to the following method.

(Synthesis of Compound 13)

The same procedure described in the synthetic method of Compound 1 was conducted except for using N-[1,1'-biphenyl]-4-yl-N-(3-bromophenyl)-1-naphthalenamine instead of Compound B to synthesize Compound 13. In addition, the chemical shift values (δ) of Compound 13 measured by $^1$H-NMR (CDCl$_3$) were 8.45-8.41 (m, 8H), 8.20 (d, 1H, J=7.80 Hz), 8.07-7.98 (m, 3H), 7.57-7.50 (m, 11H), 7.44-7.38 (m, 3H), 6.98 (d, 1H, J=7.76 Hz), 6.90-6.87 (m, 2H), 6.69 (d, 2H, J=7.82 Hz), 6.58 (d, 1H, J=7.70 Hz). From the results, the white solid thus synthesized was recognized as Compound 13.

(Synthesis of Compound 61)

The same procedure described in the synthetic method of Compound 1 was conducted except for using dibenzothiophene-3-boronic acid instead of dibenzothiophene-4-boronic acid to synthesize Compound 61. In addition, the chemical shift values (δ) of Compound 61 measured by $^1$H-NMR (CDCl$_3$) were 8.45 (d, 1H, J=7.82 Hz), 8.11-8.05 (m, 3H), 7.98 (d, 1H, J=7.68 Hz), 7.70 (s, 1H), 7.57-7.50 (m, 17H), 7.48-7.41 (m, 4H), 6.69-6.67 (m, 6H). From the results, the white solid thus synthesized was recognized as Compound 61.

(Synthesis of Compound 73)

The same procedure described in the synthetic method of Compound 1 was conducted except for using dibenzothiophene-1-boronic acid instead of dibenzothiophene-4-boronic acid to synthesize Compound 73. In addition, the chemical shift values (δ) of Compound 73 measured by $^1$H-NMR (CDCl$_3$) were 8.44 (d, 1H, J=7.80 Hz), 7.98-7.82 (m, 3H), 7.71 (s, 1H), 7.57-7.50 (m, 18H), 7.48-7.40 (m, 4H), 6.72-6.65 (m, 6H). From the results, the white solid thus synthesized was recognized as Compound 73.

Organic EL devices of Examples 1 to 4 were manufactured using Compounds 1, 13, 61, and 73 as hole transport materials prepared according to the above-described manufacturing methods.

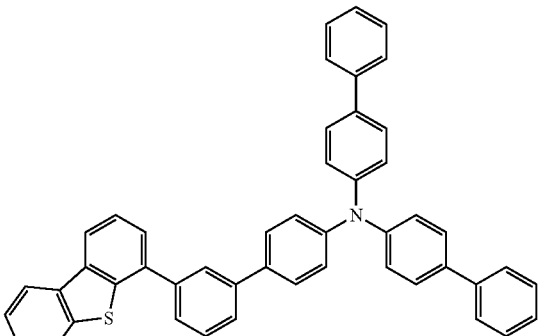

1

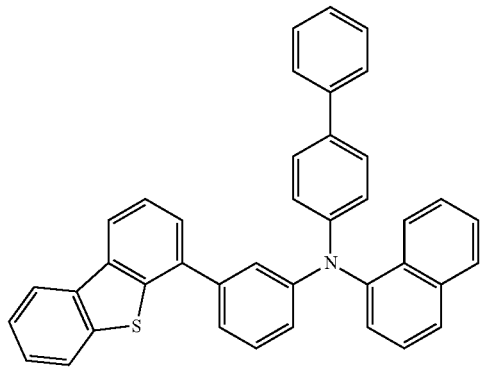

13

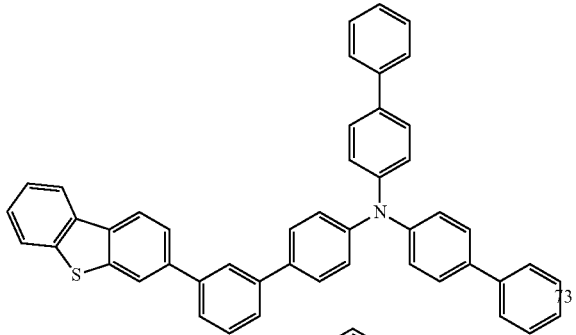

61

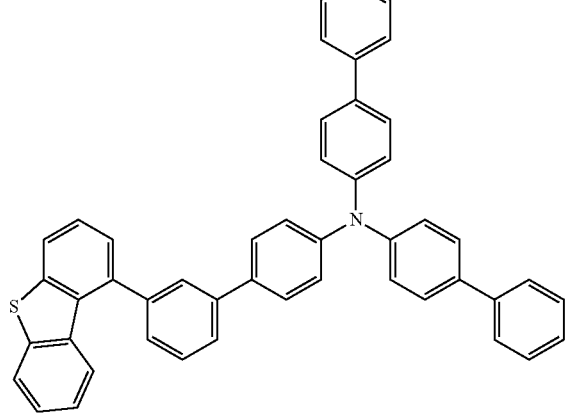

73

For comparison, organic EL devices of Comparative Examples 1 to 3 were manufactured using Compounds C1 to C3 as hole transport materials.

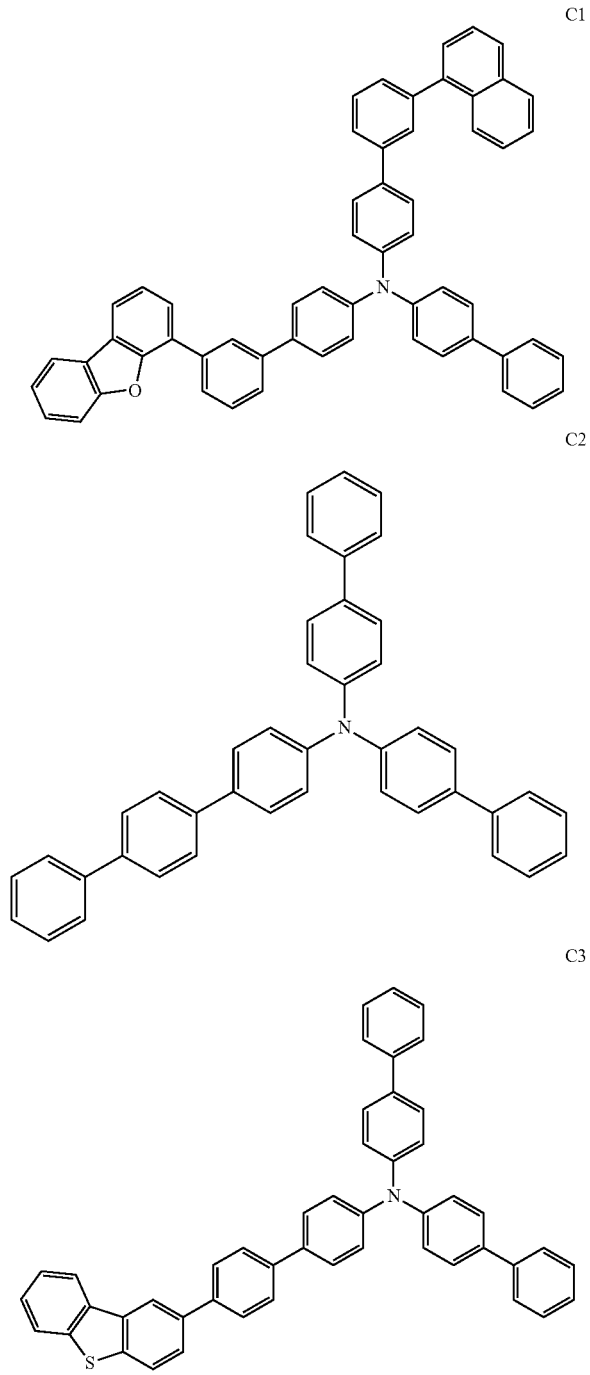

Figure 2:
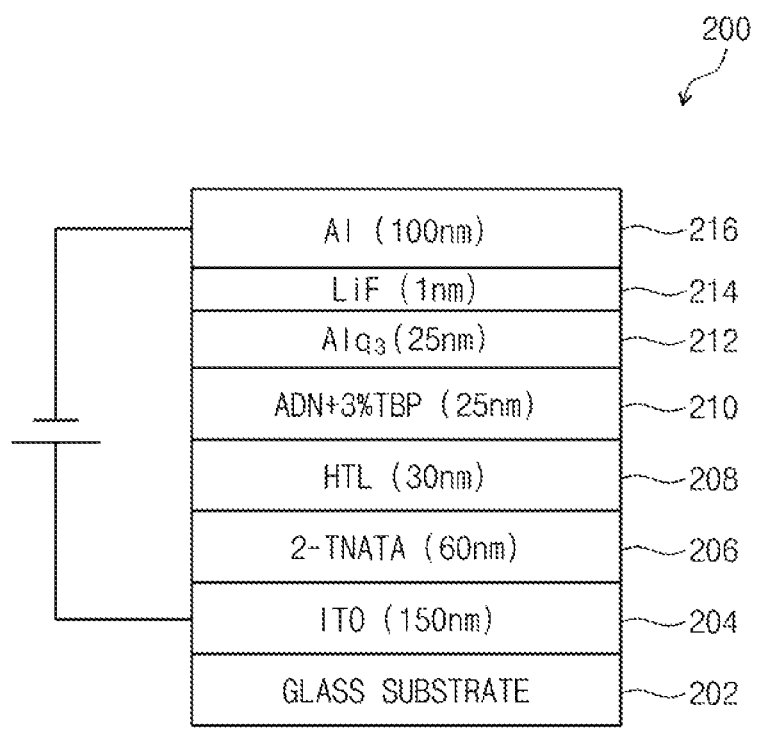
FIG. 2 illustrates a schematic diagram of an organic EL device according to an embodiment.

The organic EL device 200 according to this embodiment is shown in FIG. 2. In this embodiment, a transparent glass substrate was used as a substrate 202, an anode 204 was formed using ITO to a layer thickness of about 150 nm, a hole injection layer 206 was formed using 2-TNATA to a layer thickness of about 60 nm, a hole transport layer 208 was formed to a layer thickness of about 30 nm, an emission layer 210 was formed using ADN doped with 3% TBP to a layer thickness of about 25 nm, an electron transport layer 212 was formed using Alq3 to a layer thickness of about 25 nm, an electron injection layer 214 was formed using LiF to a layer thickness of about 1 nm, and a cathode 216 was formed using Al to a layer thickness of about 100 nm.

For the organic EL devices 200 thus manufactured, a driving voltage, emission efficiency, and half life were evaluated. Current efficiency represents a value at 10 mA/cm$^2$, and the half life represents time required for decreasing luminance from initial luminance of 1,000 cd/m$^2$ to half. The results are shown in the following Table 1.

TABLE 1

| Device manufacturing example | Hole transport layer | Voltage (V) | Emission efficiency (cd/A) | Life LT50 (h) |
| --- | --- | --- | --- | --- |
| Example 1 | Compound 1 | 6.3 | 6.7 | 2,700 |
| Example 2 | Compound 13 | 6.2 | 6.7 | 1,800 |
| Example 3 | Compound 61 | 6.2 | 6.4 | 2,200 |
| Example 4 | Compound 73 | 6.4 | 6.5 | 2,400 |
| Comparative Example 1 | Comparative Compound C1 | 6.3 | 5.8 | 1,400 |
| Comparative Example 2 | Comparative Compound C2 | 6.5 | 5.2 | 1,450 |
| Comparative Example 3 | Comparative Compound C3 | 6.5 | 6.0 | 1,100 |

Then, the glass transition temperature (Tg) was measured for Compound 1 and the following Comparative Compound C4. For the measurement of Tg, DSC7000X of Hitachi High-Technologies Corporation was used, and DSC measurement was performed. The results are shown in the following Table 2.

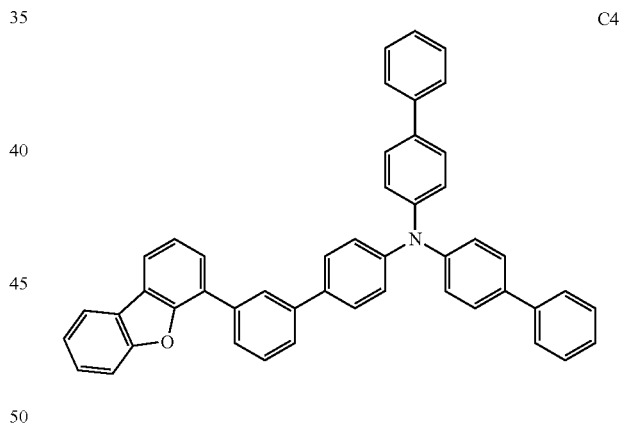

TABLE 2

| | Tg [° C.] |
| --- | --- |
| Compound 1 | 115 |
| Comparative Compound C4 | 100 |

From the results in Table 1, the organic EL device of Examples 1 to 4 using the above-described organic EL material as the hole transport material exhibited high emission efficiency and long life, when compared to those of the organic EL devices using the comparative compounds.

The organic EL material according to an embodiment introduces a dibenzothiophene part at the meta position of a phenylene group combined with amine and maintains the amine properties including long life. Due to molecular polarization owing to the effect of a sulfur atom of the dibenzothiophene, amorphous properties may improve, and even longer life and high efficiency may be attained.

In addition, the organic EL devices according to Examples 1 to 4 exhibited higher efficiency and longer life, when compared to the organic EL devices using the compounds not including dibenzothiophene (according to Comparative Examples 1 and 2). As shown in Table 2, the glass transition temperature (Tg) of Compound 1 is high, the heat resistance and the tolerance of the organic EL material of Compound 1 increased, and thus, the increase of device life may be attained.

In addition, when comparing Examples 1 to 4 to Comparative Example 3 (using

Comparative Compound 3 in which dibenzothiophene is combined at the para position of a phenylene group combined with amine via a linker), the life was improved in Examples 1 to 4. In Comparative Compound C3, the sulfur atom of the dibenzothiophene and the nitrogen atom of the amine are conjugated, thereby deteriorating the stability of radicals during carrier transportation and decreasing life. The device life of Example 2 is thought to be shorter than other device life of other Examples, because the conjugation length around amine may be short, and charge tolerance may be low. The device efficiency of Example 1 is thought to be the highest, because the dibenzothiophene is combined at position 4 with an m-phenylene group, and amorphous properties may be increased when compared to other combination positions.

The organic EL material according to an embodiment introduces a dibenzothiophene moiety at the meta position of a phenylene group with small substituent effects, combined with amine, and the amorphous properties of the material may be improved. Therefore, charge mobility may increase, and long life and high emission efficiency may be realized. Further, the organic EL material according to an embodiment may have a wide energy gap, and the application to green to red regions may be possible.

According to an embodiment, an organic EL material and an organic EL device realizing high efficiency and long life may be provided. For example, an organic EL material included in at least one layer of stacking layers between an emission layer and an anode, and an organic EL device realizing high efficiency and long life in a blue emission layer may be provided. The organic EL material according to an embodiment introduces or includes a dibenzothiophene moiety at the meta position of a phenylene group combined with the nitrogen atom (N) of an amine directly or via a linker ($L_1$), thereby improving the amorphous properties of the organic EL material and charge mobility. In addition, a glass transition temperature may increase, the heat resistance and the tolerance of the organic EL material may be improved, and an organic EL device with long life and high emission efficiency may be realized.

By way of summation and review, in the application of the organic EL device to a display, it may be desirable to increase of the emission efficiency and the life of the organic EL device. For example, in a blue emission region for a red emission region and a green emission region, it may be difficult to say that the driving voltage and the emission efficiency of the organic EL device are sufficient. To realize the high emission efficiency and the long life of the organic EL device, the normalization, the stabilization and the tolerance of a hole transport layer, etc. may be examined.

As a hole transport material used in a hole transport layer, various compounds such as an aromatic amine compound may be considered, however, some defects on device life may remain. Amine derivatives substituted with an aryl group or a heteroaryl group may be favorable materials increasing the life of an organic EL device. However, it may be difficult to say that an organic EL device using the materials have sufficient emission life. Therefore, it may be desirable for an organic EL device to exhibit higher efficiency and longer life. For example, an organic EL device may have low emission efficiency in a blue emission region when compared to a red emission region and a green emission region, and emission efficiency may be further improved.

The organic EL material according to an embodiment may introduce or include a dibenzothiophene part at the meta position of a phenylene group combined with amine directly or via L, and polarization in a molecule may be induced due to a sulfur atom of the dibenzothiophene, the amorphous properties of the material increases, and charge mobility increases, thereby realizing long life and high emission efficiency in an organic EL device. For example, remarkable effects may be attained in a blue emission region. In addition, by introducing the dibenzothiophene part at the meta position of the phenylene group combined with the amine directly or via L, the glass transition temperature of the organic EL material may increase, and the heat resistance and the tolerance of the material may be improved, thereby realizing even longer life of the organic EL device.

$Ar_1$ and $Ar_2$ may each independently be the phenyl group, the biphenyl group, the naphthyl group, the 4-(1-naphthyl)phenyl group, or the 4-(2-naphthyl)phenyl group in the organic EL material according to an embodiment, the heat resistance and the tolerance of the material may be improved, and even longer life of the organic EL device may be realized.

In the organic EL material of Formula 1 according to an embodiment, $Ar_1$, $Ar_2$ and $L_1$, $L_2$ and $L_3$ may each independently be or include a substituted or unsubstituted phenyl group or phenylene group, the conjugation of amine may be secured, and charge tolerance may be improved.

In the organic EL material according to an embodiment, a carbon at the meta position of a second phenylene group combined with amine via a first phenylene group may be combined with a carbon at position 4 of the dibenzothiophene. Thus, the planarity of an entire molecule may be broken, and amorphous properties may be improved.

In the organic EL device according to an embodiment, one of the above-mentioned organic EL materials may be included in at least one layer of stacking layers disposed between an emission layer and an anode. Thus, long life and high emission efficiency may be realized. Particularly, remarkable effects may be attained in a blue emission region.

The embodiments may provide a hole transport material for an organic electroluminescent device having high efficiency and long life.

The embodiments may provide a material for an organic EL device having high emission efficiency and long life, used in at least one layer of stacking layers disposed between an emission layer and an anode in a blue emission region, and an organic EL device including the same.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic EL material represented by the following Formula 3:

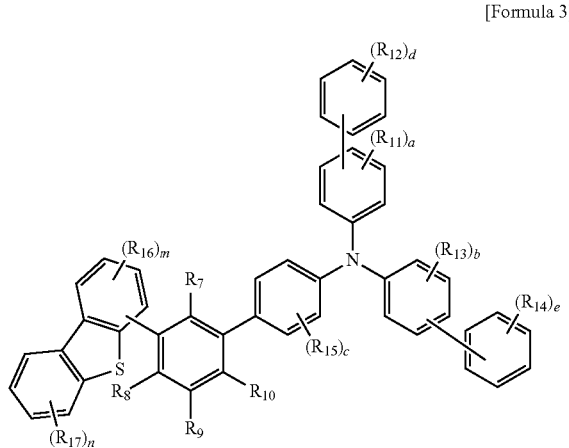

[Formula 3]

wherein, in Formula 3, $R_7$, $R_8$, $R_9$, $R_{10}$, $R_{11}$, $R_{12}$, $R_{13}$, $R_{14}$, $R_{15}$, $R_{16}$ and $R_{17}$ are each independently a substituted or unsubstituted aryl group having 6 to 30 ring carbon atoms, a substituted or unsubstituted heteroaryl group having 1 to 30 ring carbon atoms, an alkyl group having 1 to 15 carbon atoms, a silyl group, a halogen atom, a hydrogen atom, or a deuterium atom, or a combination thereof, a, b, and c are each independently an integer of 0 to 4, d and e are each independently an integer of 0 to 5, m is an integer of 0 to 3, and n is an integer of 0 to 4.

2. An organic electroluminescent (EL) device, comprising:

an anode;

an emission layer; and at least one stacking layer between the emission layer and the anode, the at least one stacking layer including an organic EL material represented by the following Formula 3:

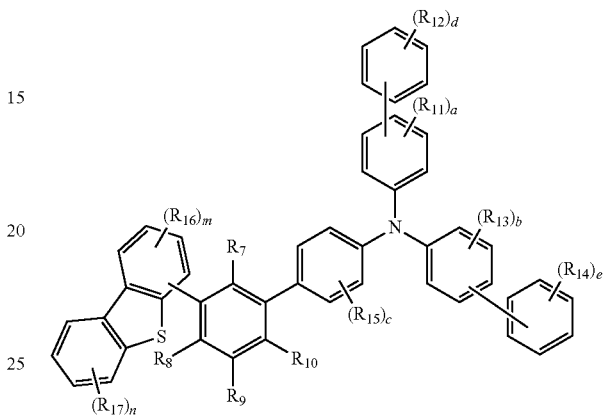

[Formula 3]

wherein, in Formula 3, $R_7$, $R_8$, $R_9$, $R_{10}$, $R_{11}$, $R_{12}$, $R_{13}$, $R_{14}$, $R_{15}$, $R_{16}$ and $R_{17}$ are each independently a substituted or unsubstituted aryl group having 6 to 30 ring carbon atoms, a substituted or unsubstituted heteroaryl group having 1 to 30 ring carbon atoms, an alkyl group having 1 to 15 carbon atoms, a silyl group, a halogen atom, a hydrogen atom, or a deuterium atom, or a combination thereof, a, b, and c are each independently an integer of 0 to 4, d and e are each independently an integer of 0 to 5, m is an integer of 0 to 3, and n is an integer of 0 to 4.

3. The organic EL device as claimed in claim 2, wherein the organic EL material represented by Formula 3 includes at least one of the following Compounds:

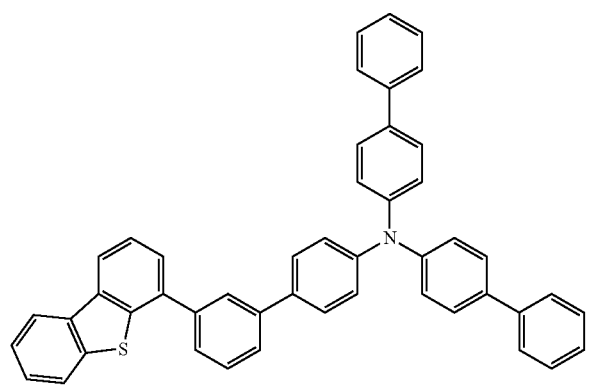

1

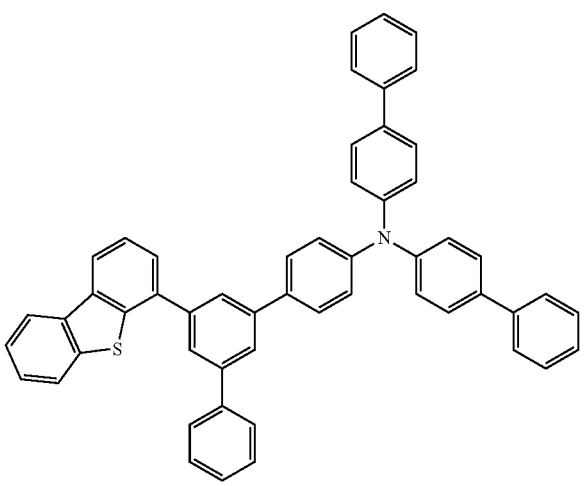

2

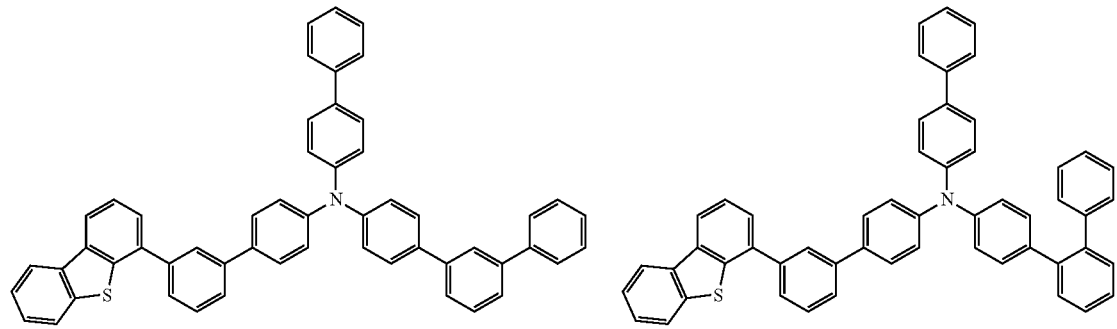
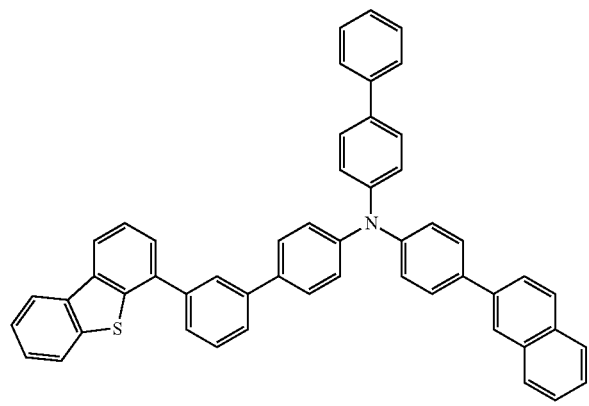
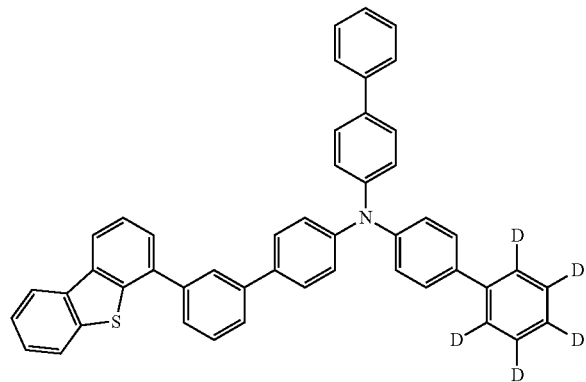
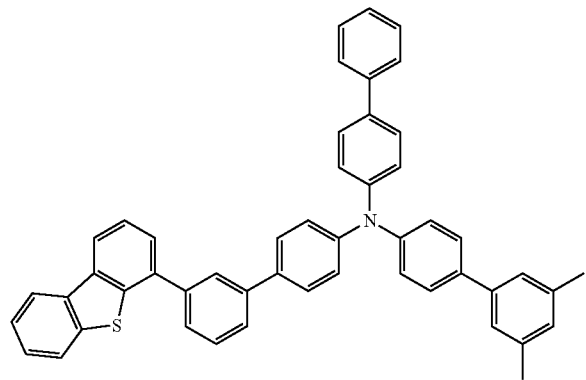

-continued
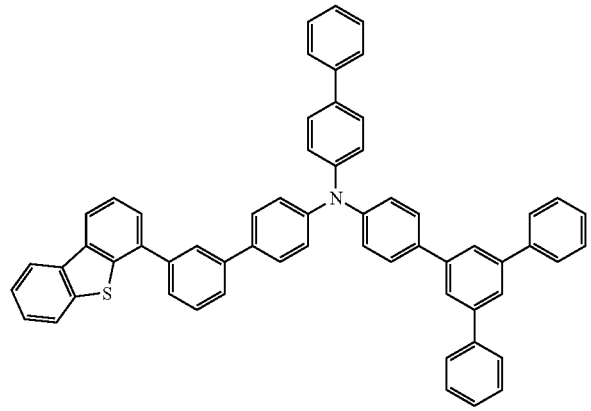
11
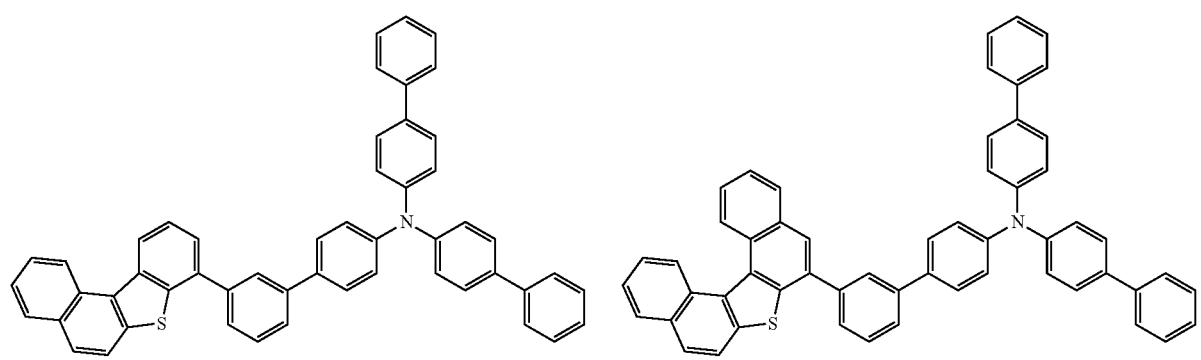
49 50
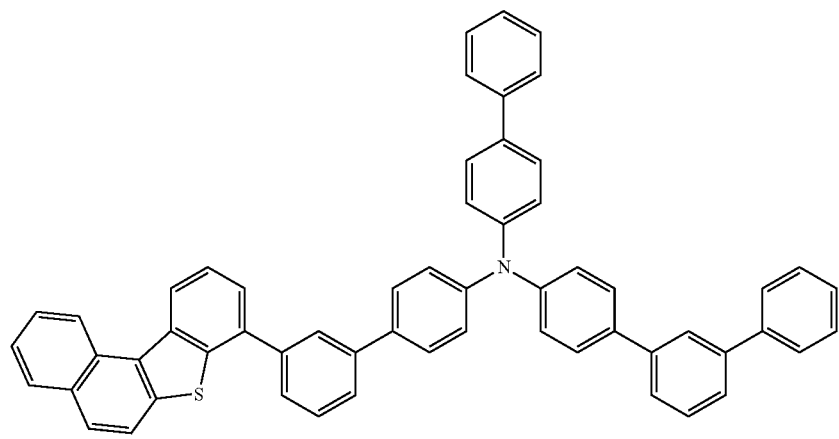
51
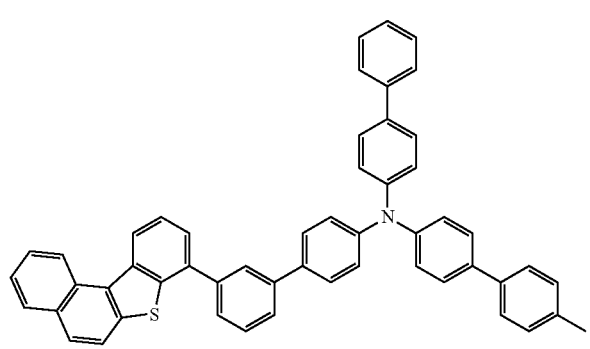
53

55
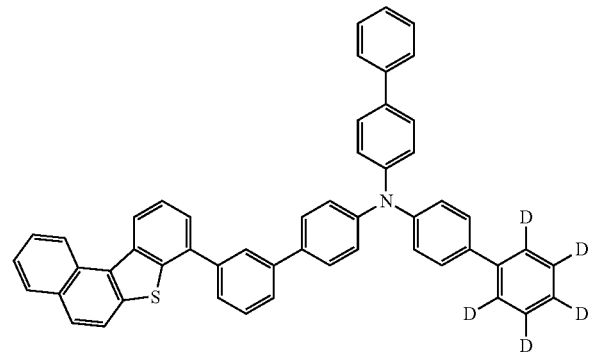
58
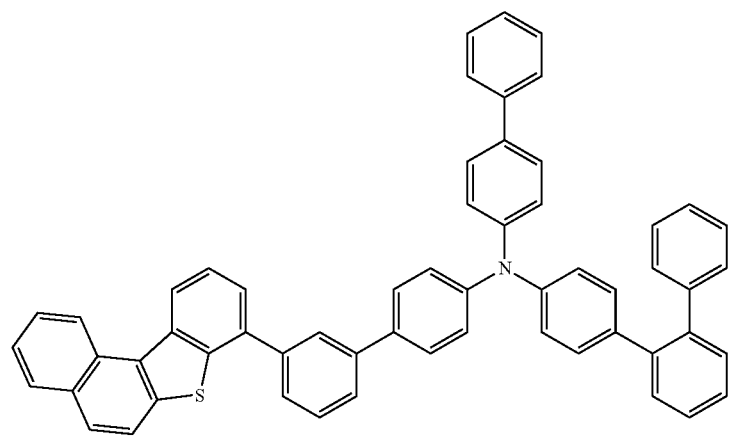
59
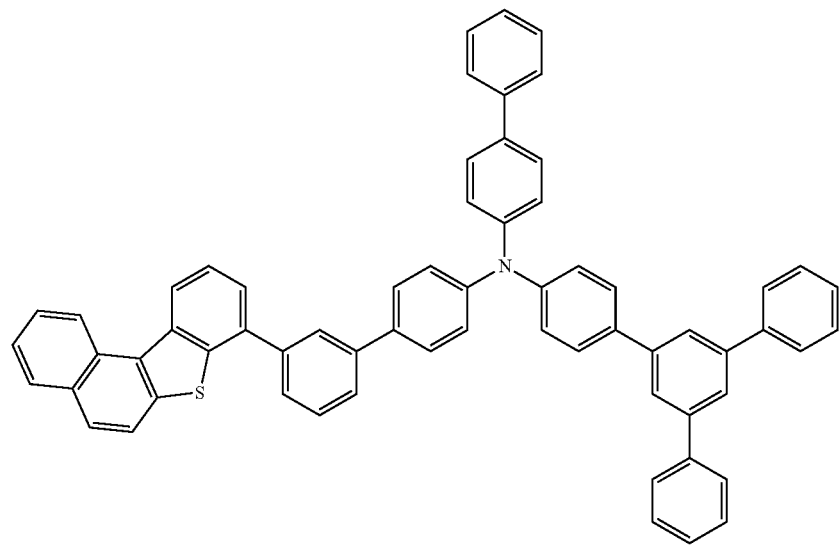

60
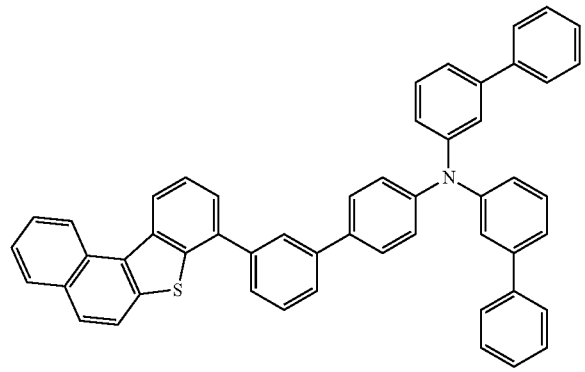
85
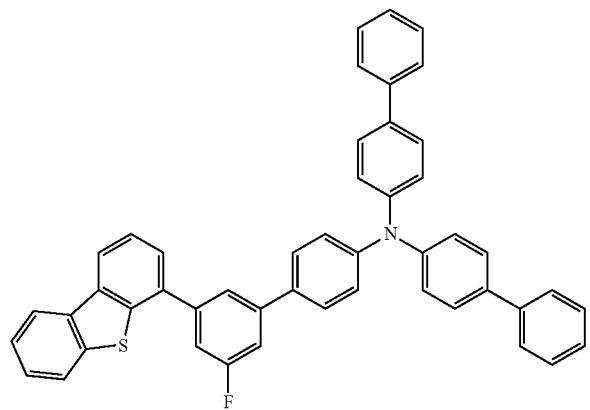
86
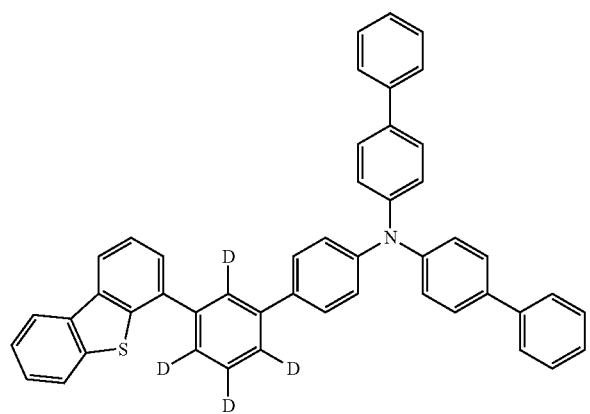
87
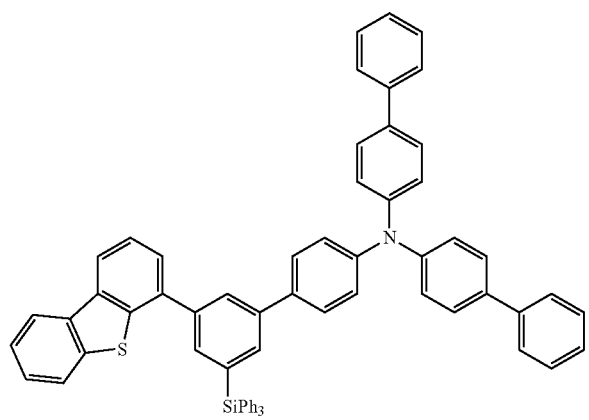
89
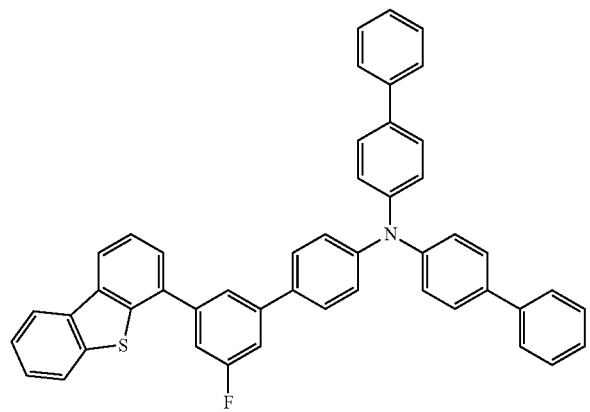

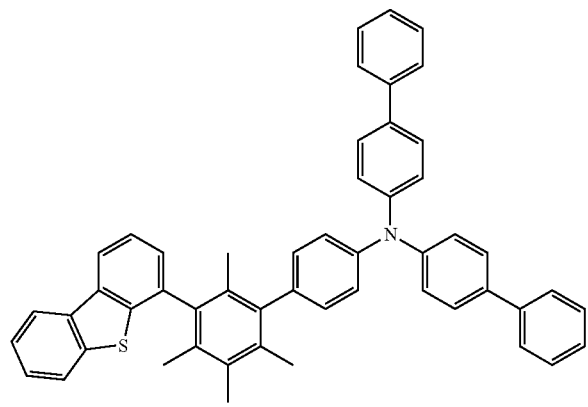
90
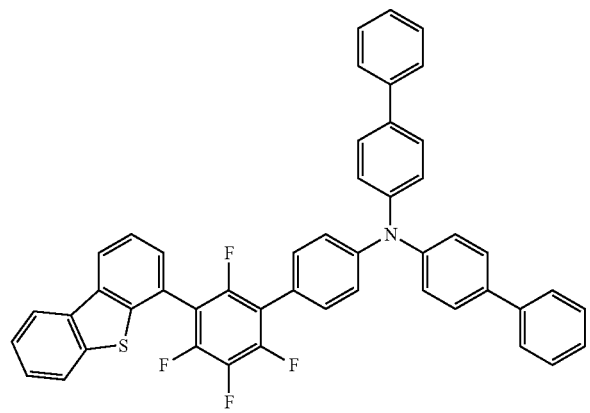
91
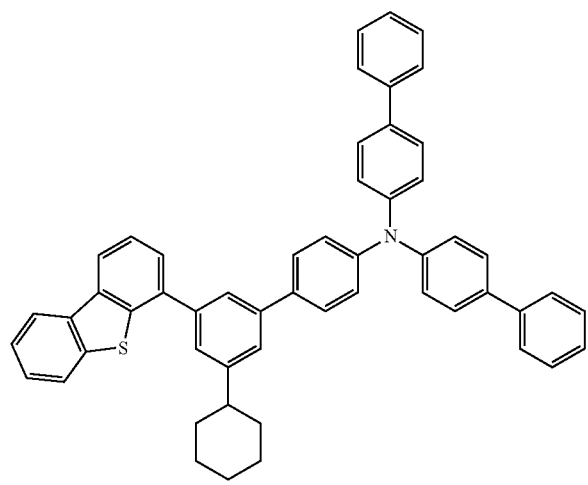
92
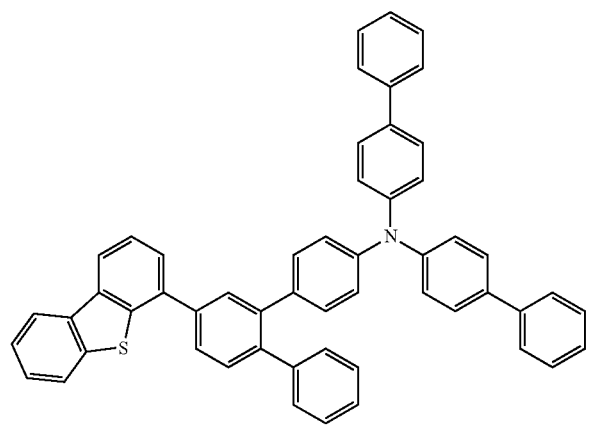
93
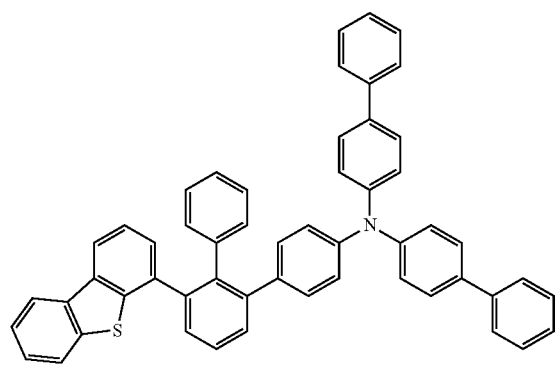
94

-continued
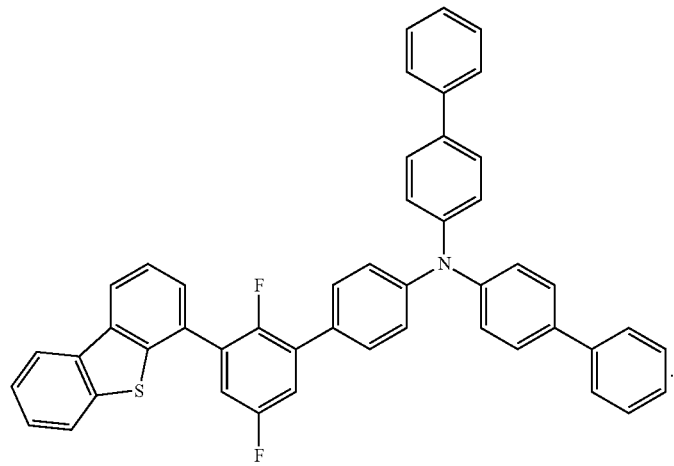
96
* * * * *